United States Patent [19]

Vazquez

[11] Patent Number: 5,216,003
[45] Date of Patent: Jun. 1, 1993

[54] DIACID-CONTAINING BENZIMIDAZOLE COMPOUNDS FOR TREATMENT OF NEUROTOXIC INJURY

[75] Inventor: Michael L. Vazquez, Gurnee, Ill.
[73] Assignee: G. D. Searle & Co., Chicago, Ill.
[21] Appl. No.: 816,207
[22] Filed: Jan. 2, 1992
[51] Int. Cl.[5] ............... A61K 31/415; C07D 233/64; C07D 403/04
[52] U.S. Cl. .................... 514/381; 514/394; 514/400; 548/113; 548/252; 548/253; 548/254; 548/306.1; 548/309.4; 548/309.7; 548/310.1
[58] Field of Search ............. 548/113, 252, 253, 254, 548/306.1, 309.4, 309.7, 310.1; 514/381, 394, 400

[56] References Cited

U.S. PATENT DOCUMENTS

| | | | |
|---|---|---|---|
| 4,141,982 | 2/1979 | Habicht et al. | 424/267 |
| 4,657,899 | 4/1987 | Rzeszotarski et al. | 558/192 |
| 4,918,064 | 4/1990 | Cordi et al. | 558/192 |

FOREIGN PATENT DOCUMENTS

| | | | |
|---|---|---|---|
| 260744 | 3/1988 | European Pat. Off. | 235/6 |
| 2737462 | 3/1978 | Fed. Rep. of Germany | 548/282 |

OTHER PUBLICATIONS

S. M. Rothman et al., *Annals of Neurology*, 19 (2), (1986).
M. N. Perkins et al., *Neuroscience Lett.*, 23, 333 (1981).
J. Davies et al., *Neuroscience Lett.*, 21, 77 (1981).
K. Matoba et al., "Structural Modification of Bioactive Compound II. Syntheses of Aminophosphonic Acids", *Chem. Pharm. Bull.*, 32 (10), 3918–3925 (1984).
D. E. Murphy et al., *J. Pharmacol. Exp. Ther.*, 240 (3), 778–784 (1987).
N. N. Vereshchagina et al., *Khim.-Farm. Zh.*, 7 (6), 18–20 (1973).
J. B. Jones et al., *Can. J. Chem.*, 55 (10), 1653–1657 (1977).
V. A. Lopyrev et al., *Magn. Reson. Chem.*, 23 (5), 305–310 (1985).
CA 113: 126606X Benzimidazoles . . . bradycardiacs, Daemmgen et al., p. 79, 1990.

*Primary Examiner*—Mary C. Lee
*Assistant Examiner*—Joseph K. McKane
*Attorney, Agent, or Firm*—J. Timothy Keane; Paul D. Matukaitis

[57] ABSTRACT

A class of diacid-containing benzimidazole compounds is described for treatment to reduce neurotoxic injury associated with anoxia or ischemia which typically follows stroke, cardiac arrest or perinatal asphyxia. The treatment includes administration of a compound of this class alone or in a composition in an amount effective as an antagonist to inhibit excitotoxic actions at major neuronal excitatory amino acid receptor sites. Compounds of most interest are those of the formula:

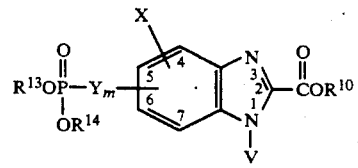

wherein $Y_m$ is —CH$_2$— or —CH$_2$—CH$_2$—; wherein m is one; wherein X is one or more groups attachable at one or more of the 4-, 5-, 6- and 7-ring positions not occupied by the phosphonoalkyl moiety; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio and amino; wherein each of $R^{10}$, $R^{13}$ and $R^{14}$ is independently selected from hydrido, alkyl, benzyl and phenyl; and wherein V is selected from hydrido and acyl; or a pharmaceutically-acceptable salt thereof.

38 Claims, No Drawings

DIACID-CONTAINING BENZIMIDAZOLE COMPOUNDS FOR TREATMENT OF NEUROTOXIC INJURY

FIELD OF THE INVENTION

This invention is in the field of clinical neurology and relates specifically to a class of compounds, compositions and methods for neuro-protective purposes such as controlling chronic or acute neurotoxic injury or brain damage resulting from neuro-degenerative diseases. For example, these compounds are particularly useful for treating neurotoxic injury which follows periods of anoxia or ischemia associated with stroke, cardiac arrest or perinatal asphyxia. The compounds would also be useful as anticonvulsants.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman et al, *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

Aminophosphonic acids have been investigated as neurotransmitter blockers [see M. N. Perkins et al, *Neuroscience Lett.*, 23, 333 (1981); and J. Davies et al, *Neuroscience Lett.*, 21, 77 (1981)]. In particular, compounds such as 2-amino-4-(2-phosphonomethyl-phenyl)butyric acid and 2-(2-amino-2-carboxy)ethylphenylphosphonic acid have been synthesized for evaluation as antagonists in blocking the action of the neurotransmitter compounds L-glutamic acid and L-aspartic acid [K. Matoba et al, "Structural Modification of Bioactive Compounds II. Syntheses of Aminophosphonic Acids", *Chem. Pharm. Bull.*, 32, (10) 3918–3925 (1984)].

An analogue of 2-amino-7-phosphonaheptanoic acid, namely 3-(2-carboxypiperazin-4-yl)propyl-1-phosphonic acid [CPP], has been reported as a potent and selective NMDA antagonist in an evaluation of CPP binding to rat brain hippocamal tissue [D. E. Murphy et al, *J. Pharmacol. Exp. Ther.*, 240 (3), 778–784 (1987)].

U.S. Pat. No. 4,657,899 to Rzeszotarski et al, which issued, describes a class of ω-[2-(phosphonoalkylenyl)-phenyl]2-aminoalkanoic acids characterized as being selective excitatory amino acid neurotransmitter receptor blockers. These compounds are mentioned for use as anticonvulsants, antiepileptics, analgesics and cognition enhancers. Typical compounds of the class include 3-[2-phosphonomethylphenyl]-2-aminopropanoic acid and 3-[2-(2-phosphonoethyl)phenyl]-2-aminopropanoic acid.

U.S. Pat. No. 4,918,064 to Cordi et al, which issued 17 Apr. 1990, describes a class of phosphonomethyl-phenylglycine compounds for treatment to reduce neurotoxic injury associated with anoxia or ischemia which typically follows stroke, cardiac arrest or perinatal asphyxia.

Several classes of acid-containing benzimidazole compounds are known which have been investigated for various pharmacological activities and pharmaceutical uses. For example, certain 2-(tetrazolyl)benzimidazole derivatives have been investigated for their tuberculostatic activity [N. N. Vereshchagina et al, *Khim.-Farm. Zh.*, 7(6), 18–20 (1973)]. Certain 2-hydroxymethylbenzimidazole-4-carboxylic acid compounds were used as models for investigation of the Asp-His-Ser charge relay system of serine proteases [J. B. Jones et al, *Can. J. Chem.*, 55(10), 1653–1657 (1977)]. German Offen. #2,737,462, published 2 Mar. 1978, describes a series of acylated benzimidazole 2-carboxylic acid compounds for use as anti-allergy agents. The transmission of substituent effects in dianion radicals of 5(6)-nitrobenzimidazole 2-carboxylic acid ethyl esters were studied by ESR spectroscopy [V. A. Lopyrev et al, *Magn. Reson. Chem.*, 25(5), 305–310 (1985)]. EP #260,744, published 23 Mar. 1988, describes a series of (1H-imidazol-1-ylmethyl)benzimidazoles as inhibitors of androgen biosynthesis.

DESCRIPTION OF THE INVENTION

Control of neuropathological processes and the neuro-degenerative consequences thereof in a subject is provided by treating the subject susceptible to neurotoxic injury with an anti-excitotoxic effective amount of a compound characterized in having activity as an antagonist at a major neuronal excitatory amino acid receptor site, such as the NMDA receptor site. Such antagonist compounds may be selected from a class of diacid-containing benzimidazole compounds, that is, compounds having an acidic group attached at the benzimidazole 2-ring position and having an acid group attached at one of the benzimidazole 4-, 5-, 6- or 7-ring positions, as defined by Formula I:

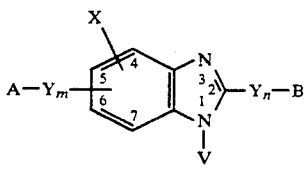 (I)

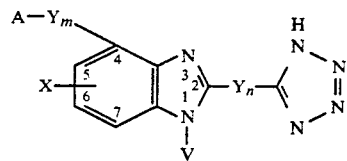 (II)

wherein each of A and B is a moiety independently selected from carboxylic acid, tetrazole and phosphorus-containing acids, and the amide, ester and salt derivatives of said acids; wherein each A moiety and B moiety may be optionally independently substituted at any substitutable position by one or more groups selected from alkyl, allyl, cycloalkyl, cycloalkylalkyl, aryl and aralkyl;

wherein each of $Y_m$ and $Y_n$ is a spacer group independently selected from one or more of alkyl, cycloalkyl and cycloalkylalkyl, any one of which spacer groups may be substituted at any substitutable position with one or more groups selected from alkyl, cycloalkyl, cycloalkylalkyl, oxo, exomethylene, halo, haloalkyl, alkenyl, cycloalkenyl, alkynyl, alkoxycarbonyl, aryl, aralkyl, hydroxy, hydroxyalkyl, alkoxy, aryloxy, alkoxyalkyl, aralkoxy, cyano, alkanoyl, alkylthio and arylthio; wherein each of m and n is a number independently selected from zero to five, inclusive;

wherein X is one or more groups attachable at one or more of the 4-, 5-, 6- and 7-ring positions of the benzimidazole ring system; wherein each X is independently selected from hydrido, halo, alkyl, cycloalkyl, cycloalkylalkyl, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, aralkylthio, cyano, cyanoamino, nitro, alkanoyl, mercapto, alkylthio, arylthio, alkylsulfinyl, arylsulfinyl, alkylsulfonyl, arylsulfonyl, and amino and amido radicals of the formula

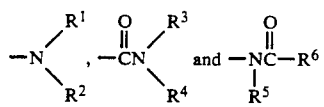

wherein each of $R^1$, $R^2$, $R^3$, $R^4$, $R^5$ and $R^6$ is independently selected from hydrido, alkyl, cycloalkyl, hydroxyalkyl, cycloalkylalkyl, alkoxyalkyl, aralkyl and aryl;

wherein V is selected from hydrido, alkyl, cycloalkyl, cycloalkylalkyl, hydroxyalkyl, alkoxyalkyl, aralkyl,

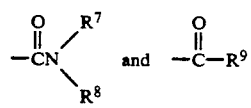

wherein each of $R^7$, $R^8$ and $R^9$ is independently selected from hydrido, alkyl, cycloalkyl, hydroxyalkyl, cycloalkylalkyl, alkoxyalkyl and aryl; and wherein $R^9$ may be further selected from alkoxy, aryloxy and aralkyloxycarbonyl;

or a pharmaceutically-acceptable salt thereof.

Within Formula I there is a preferred class consisting of compounds of Formula II wherein A is selected from

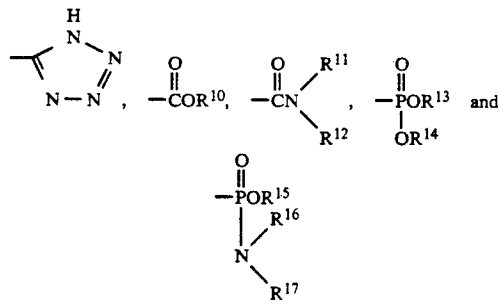

wherein each of $R^{10}$ through $R^{17}$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

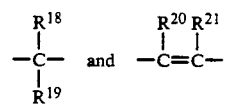

with the proviso that the total number of carbon atoms in each of $Y_m$ or $Y_n$ cannot exceed twenty carbon atoms; wherein each of $R^{18}$ and $R^{19}$ is independently selected from hydrido, alkyl, cycloalkyl, halo, haloalkyl, phenyl, benzyl, hydroxy, hydroxyalkyl, alkoxy, phenoxy, alkoxyalkyl, benzyloxy, cyano and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to four, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

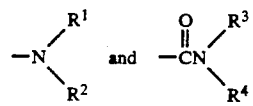

wherein each of $R^1$, $R^2$, $R^3$ and $R^4$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

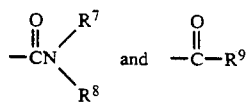 and 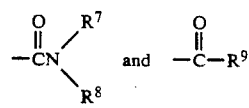

wherein each of $R^7$, $R^8$ and $R^9$ is independently selected from hydrido, alkyl, cycloalkyl, hydroxyalkyl, cycloalkylalkyl, alkoxyalkyl and aryl; and wherein $R^9$ may be further selected from alkoxy, aryloxy and aralkyloxycarbonyl;

or a pharmaceutically-acceptable salt thereof.

Within the preferred class of compounds of formula II, there is a first sub-class consisting of compounds of Formula III

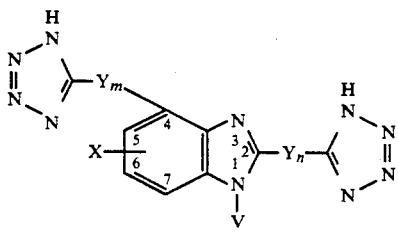 (III)

wherein each of $Y_m$ and $Y_n$ is a spacer group independently selected from one or more groups of the formula

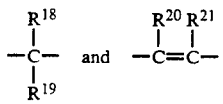

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to four, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl, wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

or a pharmaceutically-acceptable salt thereof.

Specific compounds of particular interest within Formula III are compounds, and their pharmaceutically-acceptable salts, of the group of compounds consisting of 5-methyl-2-(1H-tetrazol-5-yl)-4-[(1H-tetrazol-5-yl)methyl]benzimidazole;

2-(1H-tetrazol-5-yl)-4-[(1H-tetrazol-5-yl)methyl]benzimidazole;

6-chloro-2-(1H-tetrazol-5-yl)-4-[(1H-tetrazol-5-yl)ethyl]-benzimidazole;

6-chloro-2-(1H-tetrazol-5-yl)-4-[3-(1H-tetrazol-5-yl)propyl]-benzimidazole;

2-(1H-tetrazol-5-yl)-4-[3-(1H-tetrazol-5-yl)propyl]-benzimidazole;

5-methyl-2,4-bis(1H-tetrazol-5-yl)benzimidazole;

2,4-bis(1H-tetrazol-5-yl)benzimidazole;

6-chloro-2,4-bis(1H-tetrazol-5-yl)benzimidazole; and 5-methyl-2,4-bis(1H-tetrazol-5-yl)benzimidazole.

Within the preferred class of compounds of Formula II, there is a second sub-class consisting of compounds of Formula IV

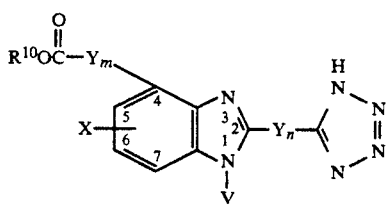 (IV)

wherein each of $Y_m$ and $Y_n$ is a spacer group independently selected from one or more groups of the formula

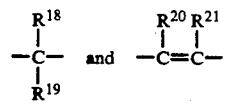

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and $$-N\begin{matrix}R^1\\\\R^2\end{matrix}$$

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl, $$-\overset{O}{\underset{}{C}}N\begin{matrix}R^7\\\\R^8\end{matrix} \quad \text{and} \quad -\overset{O}{\underset{}{C}}-R^9$$

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein $R_{10}$ is selected from hydrido, alkyl, cycloalkyl, cycloalkylalkyl, phenyl and benzyl;
or a pharmaceutically-acceptable salt thereof.

Specific compounds of particular interest within Formula IV are compounds, and their pharmaceutically-acceptable salts, of the group of compounds consisting of
2-(1H-tetrazol-5-yl)-4-benzimidazolepropanoic acid;
6-chloro-2-(1H-tetrazol-5-yl)-4-benzimidazolepropanoic acid;
6-chloro-2-(1H-tetrazol-5-yl)-4-benzimidazolebutanoic acid;
5-methyl-2-(1H-tetrazol-5-yl)-4-benzimidazoleacetic acid; and
2-(1H-tetrazol-5-yl)-4-benzimidazoleacetic acid.

Within the preferred class of compounds of Formula II, there is a third sub-class consisting of compounds of Formula V (V)

wherein each of $Y_m$ and $Y_n$ is a spacer group independently selected from one or more groups of the formula $$-\overset{R^{18}}{\underset{R^{19}}{C}}- \quad \text{and} \quad -\overset{R^{20}}{C}=\overset{R^{21}}{C}-$$

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;
wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and $$-N\begin{matrix}R^1\\\\R^2\end{matrix}$$

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl, $$-\overset{O}{\underset{}{C}}N\begin{matrix}R^7\\\\R^8\end{matrix} \quad \text{and} \quad -\overset{O}{\underset{}{C}}-R^9$$

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein each of $R^{15}$, $R^{16}$ and $R^{17}$ is independently selected from hydrido, alkyl, cycloalkyl, cycloalkylalkyl, phenyl and benzyl;
or a pharmaceutically-acceptable salt thereof.

Specific compounds of particular interest within Formula V are compounds, and their pharmaceutically-acceptable salts, of the group of compounds consisting of
5-methyl-2-(1H-tetrazol-5-yl)-4-benzimidazolemethylphosphonamide;
2-(1H-tetrazol-5-yl)-4-benzimidazolemethylphosphonamide;
6-chloro-2-(1H-tetrazol-5-yl)-4-benzimidazole-ethylphosphonamide;
2-(1H-tetrazol-5-yl)-4-benzimidazoleethylphosphonamide;
6-chloro-2-(1H-tetrazol-5-yl)-4-benzimidazolepropylphosphonamide;
2-(1H-tetrazol-5-yl)-4-benzimidazolepropylphosphonamide;
2-(1H-tetrazol-5-yl)-4-benzimidazolephosphonamide; and
5-methyl-2-(1H-tetrazol-5-yl)-4-benzimidazoleethylphosphonamide.

Within the preferred class of compounds of Formula II, there is a fourth sub-class consisting of compounds of Formula VI

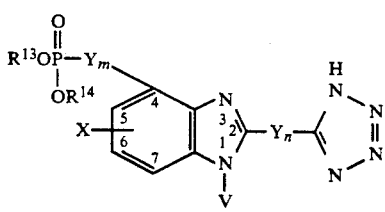
(VI)

wherein each of $Y_m$ and $Y_n$ is a spacer group independently selected from one or more groups of the formula

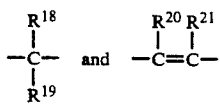

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

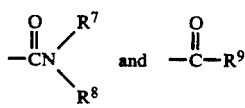

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein each of $R^{13}$ and $R^{14}$ is independently selected from hydrido, alkyl, cycloalkyl, cycloalkylalkyl, phenyl and benzyl;
or a pharmaceutically-acceptable salt thereof.

Specific compounds of particular interest within Formula VI are compounds, and their pharmaceutically-acceptable salts, of the group of compounds consisting of
[5-methyl-2-(1H-tetrazol-5-yl)benzimidazole]-4-methylphosphonic acid;
[2-(1H-tetrazol-5-yl)benzimidazole]-4-methylphosphonic acid;
[6-chloro-2-(1H-tetrazol-5-yl)benzimidazole]-4-ethylphosphonic acid;
[2-(1H-tetrazol-5-yl)benzimidazole]-4-ethylphosphonic acid;
[6-chloro-2-(1H-tetrazol-5-yl)benzimidazole]-4-propylphosphonic acid;
[2-(1H-tetrazol-5-yl)benzimidazole]-4-propylphosphonic acid;
[2-(1H-tetrazol-5-yl)benzimidazole]-4-phosphonic acid; and
[5-methyl-2-(1H-tetrazol-5-yl)benzimidazole]-4-ethylphosphonic acid.

With formula I there is another preferred class consisting of compounds of Formula VII

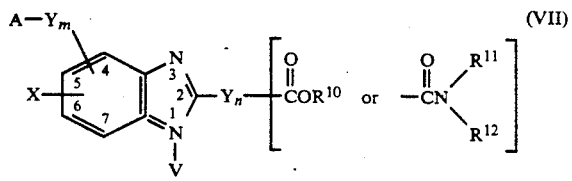
(VII)

wherein A is selected from

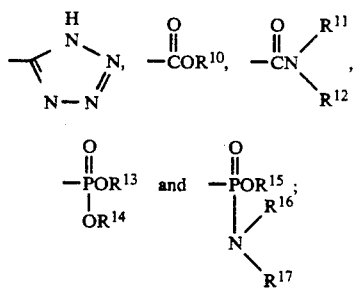

wherein each of $R^{10}$ through $R^{17}$ is independently selected from hydrido, alkyl, allyl, cycloalkyl, cycloalkylalkyl, phenyl and benzyl;
wherein each of $Y_m$ and $Y_n$ is a spacer group independently selected from one or more groups of the formula

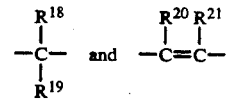

with the proviso that the total number of carbon atoms in each of $Y_m$ or $Y_n$ cannot exceed twenty carbon atoms; wherein each of $R^{18}$ and $R^{19}$ is independently selected from hydrido, alkyl, cycloalkyl, halo, haloalkyl, phenyl, benzyl, hydroxy, hydroxyalkyl, alkoxy, phenoxy, alkoxyalkyl, benzyloxy, cyano and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to three, inclusive;

wherein X is one or more groups attachable at one or more of the 4-, 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

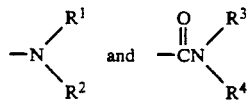

wherein each of $R^1$, $R^2$, $R^3$ and $R^4$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

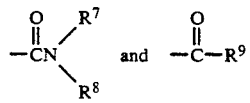

wherein each of $R^7$, $R^8$ and $R^9$ is independently selected from hydrido, alkyl, cycloalkyl, hydroxyalkyl, cycloalkyl, alkoxyalkyl and aryl; and wherein $R^9$ may be further selected from alkoxy, aryloxy and aralkyloxycarbonyl;

or a pharmaceutically-acceptable salt thereof.

Within the preferred class of compounds of Formula VII, there is a first sub-class consisting of compounds of Formula VIII

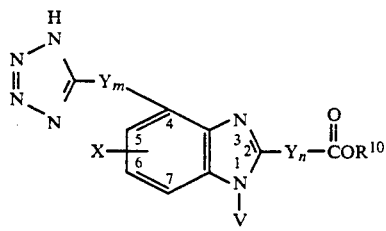

wherein each of $Y_m$ and $Y_n$ is a spacer group independently selected from one or more groups of the formula

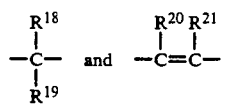

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

wherein each of $R^1$ and $R^2$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

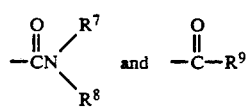

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein $R^{10}$ is selected from hydrido, alkyl, cycloalkyl, cycloalkylalkyl, phenyl and benzyl;

or a pharmaceutically-acceptable salt thereof.

Specific compounds of particular interest within Formula VIII are compounds, and their pharmaceutically-acceptable salts, of the group of compounds consisting of 5-methyl-4-[(1H-tetrazol-5-yl)methyl]benzimidazole-2-carboxylic acid;

4-[(1H-tetrazol-5-yl)methyl]benzimidazole-2-carboxylic acid;

6-chloro-4-[2-(1H-tetrazol-5-yl)ethyl]benzimidazole-2-carboxylic acid;

6-chloro-4-[2-(1H-tetrazol-5-yl)ethyl]benzimidazole-2-carboxylic acid;

4-[2-(1H-tetrazol-5-yl)ethyl]benzimidazole-2-carboxylic acid;

4-[3-(1H-tetrazol-5-yl)propyl]benzimidazole-2-carboxylic acid;

6-chloro-4-[3-(1H-tetrazol-5-yl)propyl]benzimidazole-2-carboxylic acid;

5-methyl-4-(1H-tetrazol-5-yl)benzimidazole-2-carboxylic acid;

4-(1H-tetrazol-5-yl)benzimidazole-2-carboxylic acid.

Within the preferred class of compounds of Formula VII, there is a second sub-class consisting of compounds of Formula IX

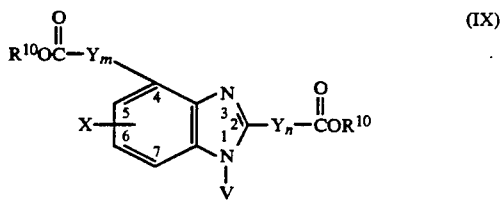

wherein each of $Y_m$ and $Y_n$ is a spacer group independently selected from one or more groups of the formula

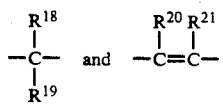

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

wherein each of $R^1$ and $R^2$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

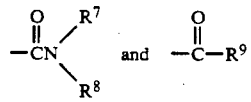

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein $R^{10}$ is selected from hydrido, alkyl, cycloalkyl, cycloalkylalkyl, phenyl and benzyl;

or a pharmaceutically-acceptable salt thereof.

Specific compounds of particular interest within Formula IX are compounds, and their pharmaceutically-acceptable salts, of the group of compounds consisting of 5-methyl-2-carboxy-4-benzimidazoleacetic acid;
2-carboxy-4-benzimidazoleacetic acid;
6-chloro-2-carboxy-4-benzimidazolepropanoic acid;
2-carboxy-4-benzimidazolepropanoic acid;
6-chloro-2-carboxy-4-benzimidazolebutanoic acid;
2-carboxy-4-benzimidazolebutanoic acid;
5-methyl-2,4-benzimidazoledicarboxylic acid; and
2,4-benzimidazoledicarboxylic acid.

Within the preferred class of compounds of Formula VII, there is a third sub-class consisting of compounds of Formula X

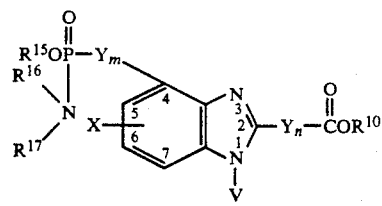

wherein each of $Y_m$ and $Y_n$ is a spacer group independently selected from one or more groups of the formula

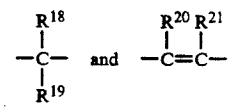

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

wherein each of $R^1$ and $R^2$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

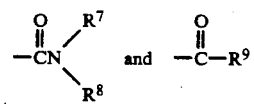

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein each of $R^{10}$, $R^{15}$, $R^{16}$ and $R^{17}$ is independently selected from hydrido, alkyl, allyl, cycloalkyl, cycloalkylalkyl, phenyl and benzyl;

or a pharmaceutically-acceptable salt thereof.

Specific compounds of particular interest within Formula X are compounds, and their pharmaceutically-acceptable salts, of the group of compounds consisting of 4-(phosphonamidomethyl)benzimidazole-2-carboxylic acid;

ethyl 4-[2-(ethoxyphosphonamido)ethyl]benzimidazole-2-carboxylate;

4-(phosphonamidoethyl)benzimidazole-2-carboxylic acid;

ethyl 6-chloro-4-[(ethoxyphosphonamide)methyl]benzimidazole-2-carboxylate;

6-chloro-4-(phosphonamidomethyl)benzimidazole-2-carboxylic acid;

ethyl 5-methyl-4-[(ethoxyphosphonamido)methyl]-benzimidazole-2-carboxylate;

5-methyl-4-(phosphonamidomethyl)benzimidazole-2-carboxylic acid;

ethyl 6-chloro-5-methyl-4-[(ethoxyphosphonamido)methyl]-benzimidazole-2-carboxylate;

6-chloro-5-methyl-4-(phosphonamidomethyl)-benzimidazole-2-carboxylic acid;

ethyl 4-(ethoxyphosphonamido)benzimidazole-2-carboxylate;

ethyl 4-(ethoxyphosphonamido)benzimidazole-2-carboxylate, monohydrochloride;

4-phosphonamidobenzimidazole-2-carboxylic acid;

ethyl 4-[2-(ethoxyphosphonamido)-E-ethenyl]benzimidazole-2-carboxylate;

4-(2-phosphonamido-E-ethenyl)benzimidazole-2-carboxylic acid; and 4-(2-phosphonamidoethyl)benzimidazole-2-carboxylic acid.

Within the preferred class of compounds of Formula VII, there is a fourth sub-class consisting of compounds of Formula XI

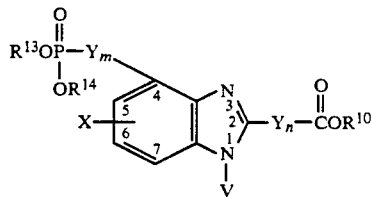

(XI)

wherein each of $Y_m$ and $Y_n$ is a spacer group independently selected from one or more groups of the formula

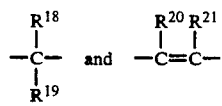

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

wherein each of $R^1$ and $R^2$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

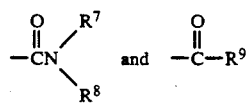

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein each of $R^{10}$, $R^{13}$ and $R^{14}$ is independently selected from hydrido, alkyl, allyl, cycloalkyl, cycloalkylalkyl, phenyl and benzyl;

or a pharmaceutically-acceptable salt thereof.

Specific compounds of particular interest within Formula XI are compounds, and their pharmaceutically-acceptable salts, of the group of compounds consisting of 4-(phosphonomethyl)benzimidazole-2-carboxylic acid;

ethyl 4-[(diethoxyphosphonyl)ethyl]benzimidazole-2-carboxylate;

4-(phosphonoethyl)benzimidazole-2-carboxylic acid;

ethyl 6-chloro-4-[(diethoxyphosphonyl)methyl]benzimidazole-2-carboxylate;

6-chloro-4-(phosphonomethyl)benzimidazole-2-carboxylic acid;

ethyl 5-methyl-4-[(diethoxyphosphonyl)methyl]benzimidazole-2-carboxylate;

5-methyl-4-(phosphonomethyl)benzimidazole-2-carboxylic acid;

ethyl 6-chloro-5-methyl-4-[(ethoxyphosphonyl)methyl]-benzimidazole-2-carboxylate;

5-methyl-4-(phosphonomethyl)benzimidazole-2-carboxylic acid;

ethyl 4-(diethoxyphosphonyl)benzimidazole-2-carboxylate; ethyl 4-(diethoxyphosphonyl)benzimidazole-2-carboxylate, monohydrochloride;

4-phosphonobenzimidazole-2-carboxylic acid;

ethyl 4-[2-(diethoxyphosphonyl)-E-ethenyl]benzimidazole-2-carboxylate;

4-(2-phosphono-E-ethenyl)benzimidazole-2-carboxylic acid; and 4-(2-phosphonoethyl)benzimidazole-2-carboxylic acid.

Within the preferred class of compounds of Formula VII, there is a fifth sub-class consisting of compounds of Formula XII

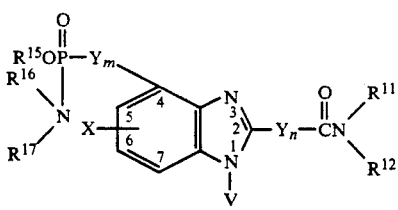 (XII)

wherein each of $Y_m$ and $Y_n$ is a spacer group independently selected from one or more groups of the formula

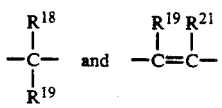

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

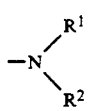

wherein each of $R^1$ and $R^2$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

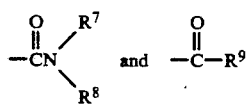

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein each of $R^{11}$, $R^{12}$, $R^{15}$, $R^{16}$ and $R^{17}$ is independently selected from hydrido, alkyl, allyl, cycloalkyl, cycloalkylalkyl, phenyl and benzyl;

or a pharmaceutically-acceptable salt thereof.

Specific compounds of particular interest within Formula XII are compounds, and their pharmaceutically-acceptable salts, of the group of compounds consisting of 4-(phosphonamidomethyl)benzimidazole-2-carboxamide;

ethyl 4-[(ethoxyphosphonamido)ethyl]benzimidazole-2-carboxamide;

4-(phosphonamidoethyl)-benzimidazole-2-carboxamide;

6-chloro-4-(phosphonamidomethyl)benzimidazole-2-carboxamide;

ethyl 5-methyl-4-[(ethoxyphosphonamido)methyl]benzimidazole-2-carboxamide;

5-methyl-4-(phosphonamidomethyl)benzimidazole-2-carboxamide;

ethyl 6-chloro-5-methyl-4-[(ethoxyphosphonamido)methyl]-benzimidazole-2-carboxamide;

6-chloro-5-methyl-4-(phosphonamidomethyl)benzimidazole-2-carboxamide;

ethyl 4-(ethoxyphosphonamido)benzimidazole-2-carboxamide;

ethyl 4-(ethoxyphosphonamido)benzimidazole-2-carboxamide, monohydrochloride;

4-phosphonamidobenzimidazole-2-carboxamide;

ethyl 4-[2-(ethoxyphosphonamido)-E-ethenyl]benzimidazole-2-carboxamide;

4-(2-phosphonamido-E-ethenyl)benzimidazole-2-carboxamide; and 4-(2-phosphonamidoethyl)benzimidazole-2-carboxamide.

Within the preferred class of compounds of Formula VII, there is a sixth sub-class consisting of compounds of Formula XIII

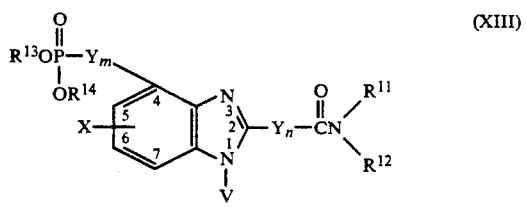 (XIII)

wherein each of $Y_m$ and $Y_n$ is a spacer group independently selected from one or more groups of the formula

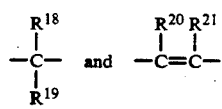

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

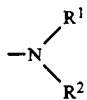

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

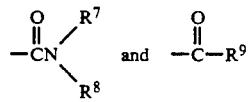

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein each of $R^{11}$, $R^{12}$, $R^{13}$ and $R^{14}$ is independently selected from hydrido, alkyl, allyl, cycloalkyl, cycloalkylalkyl, phenyl and benzyl;
or a pharmaceutically-acceptable salt thereof.

Specific compounds of particular interest within Formula XIII are compounds, and their pharmaceutically-acceptable salts, of the group of compounds consisting of
4-(phosphonomethyl)benzimidazole-2-carboxamide;
4-[2-(diethoxyphosphonyl)ethyl]benzimidazole-2-carboxamide;
4-(2-phosphonoethyl)benzimidazole-2-carboxamide;
6-chloro-4-[(diethoxyphosphonyl)methyl]benzimidazole-2-carboxamide;
6-chloro-4-(phosphonomethyl)benzimidazole-2-carboxamide;
5-methyl-4-[(diethoxyphosphonyl)methyl]benzimidazole-2-carboxamide;
5-methyl-4-(phosphonomethyl)benzimidazole-2-carboxamide;
6-chloro-5-methyl-4-[(diethoxyphosphonyl)methyl]-benzimidazole-2-carboxamide;
6-chloro-5-methyl-(phosphonomethyl)benzimidazole-2-carboxamide;
4-(diethoxyphosphonyl)benzimidazole-2-carboxamide;
4-(diethoxyphosphonyl)benzimidazole-2-carboxamide, monohydrochloride;
4-phosphonobenzimidazole-2-carboxamide;
4-[2-(diethoxyphosphonyl)-E-ethenyl]benzimidazole-2-carboxamide;
4-(2-phosphono-E-ethenyl)benzimidazole-2-carboxamide; and
4-(2-phosphonoethyl)benzimidazole-2-carboxamide.

Within the preferred class of compounds of Formula VII, there is a seventh sub-class consisting of compounds of Formula XIV

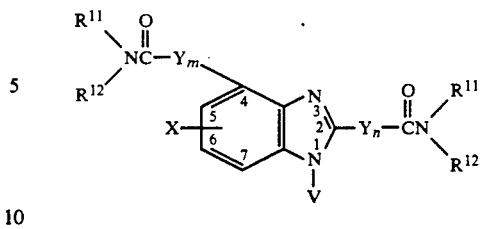

wherein each of $Y_m$ and $Y_n$ is a spacer group independently selected from one or more groups of the formula

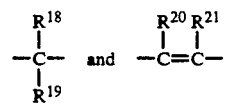

with the proviso that the total number of carbon atoms in each of $Y_m$ or $Y_n$ cannot exceed ten carbon atoms;
wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;
where X is one or more groups attachable at one or more of the 5-, 6- and 7-ring positions of the benzimidazole ring system; wherein each X is independently selected from hydrido, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio and arylthio,

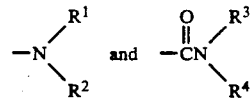

wherein each of $R^1$, $R^2$, $R^3$ and $R^4$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

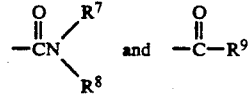

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein each of $R^{11}$ and $R^{12}$ is independently selected from hydrido, alkyl, allyl, cycloalkyl, cycloalkylalkyl, phenyl and benzyl;
or a pharmaceutically-acceptable salt thereof.

Specific compounds of particular interest within Formula XIV are compounds, and their pharmaceutically-acceptable salts, of the group of compounds consisting of
5-methyl-2-carboxamidobenzimidazole-4-acetamide;
2-carboxamidobenzimidazole-4-acetamide;
6-chloro-2-carboxamidobenzimidazole-4-propanamide;
2-carboxamidobenzimidazole-4-propanamide;
6-chloro-2-carboxamidobenzimidazole-4-butanamide;
2-carboxamidobenzimidazole-4-butanamide;
5-methylbenzimidazole-2,4-dicarboxamide; and
benzimidazole-2,4-dicarboxamide.

Within the preferred class of compounds of Formula VII, there is a eighth sub-class consisting of compounds of Formula XV

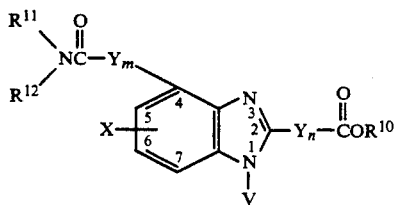

wherein each of $Y_m$ and $Y_n$ is a spacer group independently selected from one or more groups of the formula

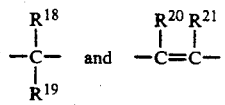

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to three, inclusive;
wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio and arylthio,

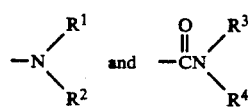

wherein each of $R^1$, $R^2$, $R^3$ and $R^4$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

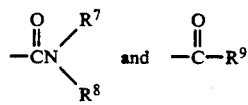

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein each of $R^{10}$, $R^{11}$ and $R^{12}$ is independently selected from hydrido, alkyl, cycloalkyl, cycloalkylalkyl, phenyl and benzyl;
or a pharmaceutically-acceptable salt thereof.

Specific compounds of particular interest within Formula XV are compounds, and their pharmaceutically-acceptable salts, of the group of compounds consisting of
5-methyl-4-acetamidobenzimidazole-2-carboxylic acid;
4-acetamidobenzimidazole-2-carboxylic acid;
6-chloro-4-propanamidobenzimidazole-2-carboxylic acid;
4-propanamidobenzimidazole-2-carboxylic acid;
6-chloro-4-butanamidobenzimidazole-2-carboxylic acid; and
4-butanamidobenzimidazole-2-carboxylic acid.

The term "hydrido" denotes a single hydrogen atom (H). This hydrido group may be attached, for example, to an oxygen atom to form a hydroxyl group; or, as another example, one hydrido group may be attached to a carbon atom to form a >C— group; or, as another example, two hydrido groups may be attached to a carbon atom to form a —CH$_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from ethyl, methyl and fluoro. Specifically embraced by the term "haloalkyl" are monohaloalkyl, dihaloalkyl and polyhaloalkyl groups. A monohaloalkyl group, for example, may have either a ethyl, a methyl, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two methyl atoms, such as a dimethylmethyl group, or one fluoro atom and one methyl atom, such as a fluoro-methyl-methyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, methyl or ethyl, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenyl-ethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. For any of the foregoing defined radicals, preferred radicals are those containing from one to about ten carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Compounds of Formula I would be useful in control of neuropathological processes and the neuro-degenerative consequences thereof by administering a therapeutically-effective amount of a compound of Formula I to a subject in need of such control or treatment. A compound of Formula I would be useful alone, or in a composition containing one or more pharmaceutical excipients, for neuro-protective purposes such as for controlling or treating chronic or acute neurotoxic injury or brain damage resulting from a neuro-degenerative disease. Compounds of Formula I would be particularly useful for treating neurotoxic injury which follows periods of anoxia or hypoxia producing ischemia typically associated with stroke, cardiac arrest or perinatal asphyxia. The phrase "therapeutically-effective amount" of a compound of Formula I is defined as that amount of compound which produces an efficacious response in a subject afflicted with or susceptible to a neuro-degenerative disease or neurotoxic injury.

In Formula I, as well as in Formulae II-XV defining sub-sets of compounds within Formula I, there is shown a diacid-containing benzimidazole ring system. Within the six-membered ring portion of this benzimidazole ring system, there are substitutable positions at the 4-, 5-, 6- and 7-ring positions. In each of Formulae I-XV, there is a requirement for attachment of an acidic moiety at one of the 4-, 5-, 6- or 7-ring positions. This acidic moiety may be provided by a carboxylic acid, tetrazole, or phosphorus-containing acid, or by the amide, ester or salt derivatives of such acids which when hydrolyzed would provide the acidic moiety. It is preferred that the acidic moiety be attached to the ring position through an alkylene group such as —$CH_2$— or —$CH_2CH_2$—. Favored positions for attachment of the acidic moiety are the 4-, 5- and 7-ring positions. The most favored position for attachment of the acidic moiety is at the 4-ring position. An X substituent, selected as defined above, may be attached at one or more of the 4-, 5-, 6- or 7-ring positions not occupied by the acidic moiety.

Also included in the family of compounds of Formula I are isomeric forms including geometric isomers and diastereoisomers, including enantiomers, and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, methylprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I–IV, wherein the A, B, R, V, $Y_m$ and $Y_n$ substituents are as defined for Formula I, above, except where further noted.

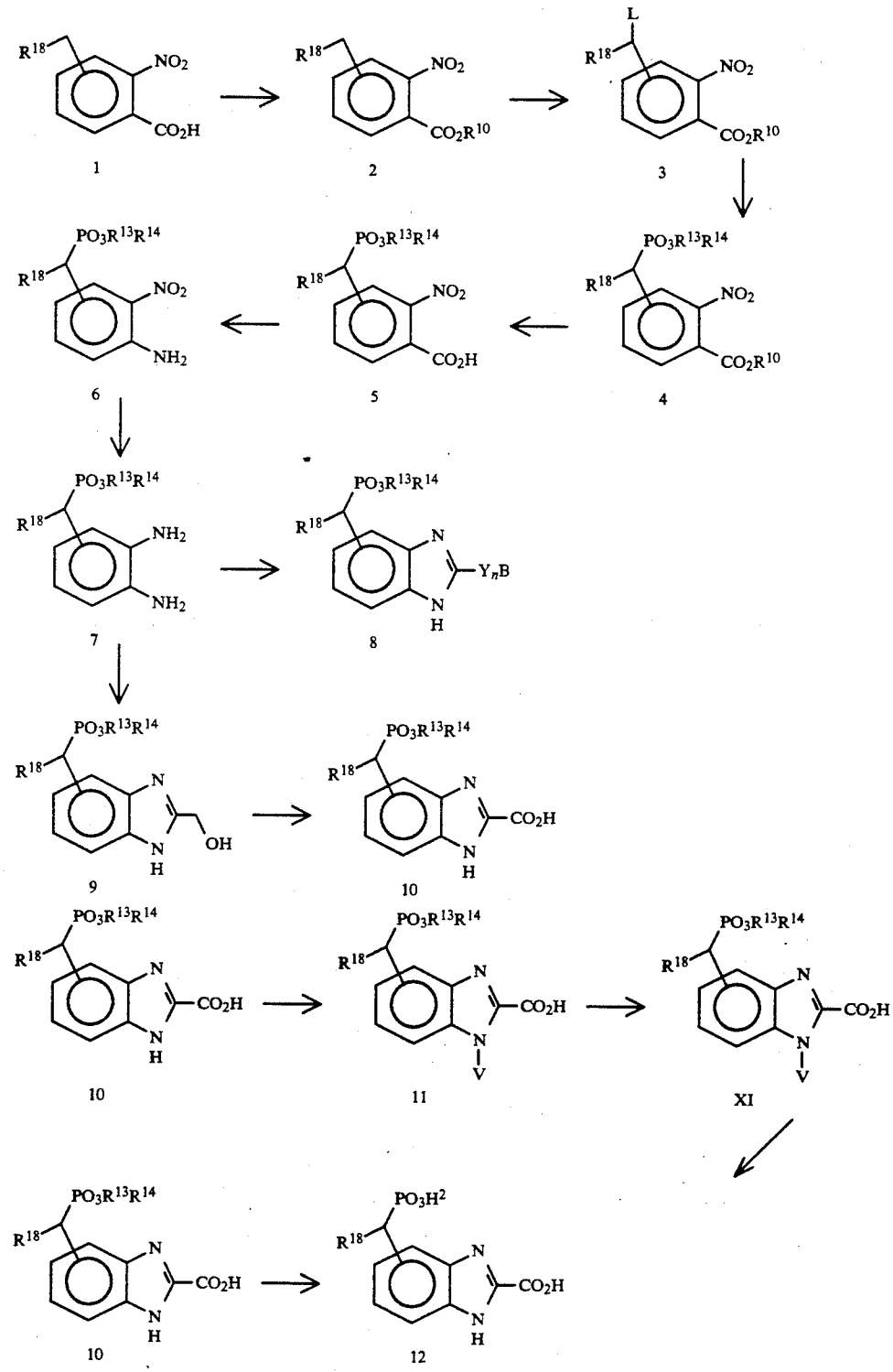

Scheme I 5,216,003
Scheme II
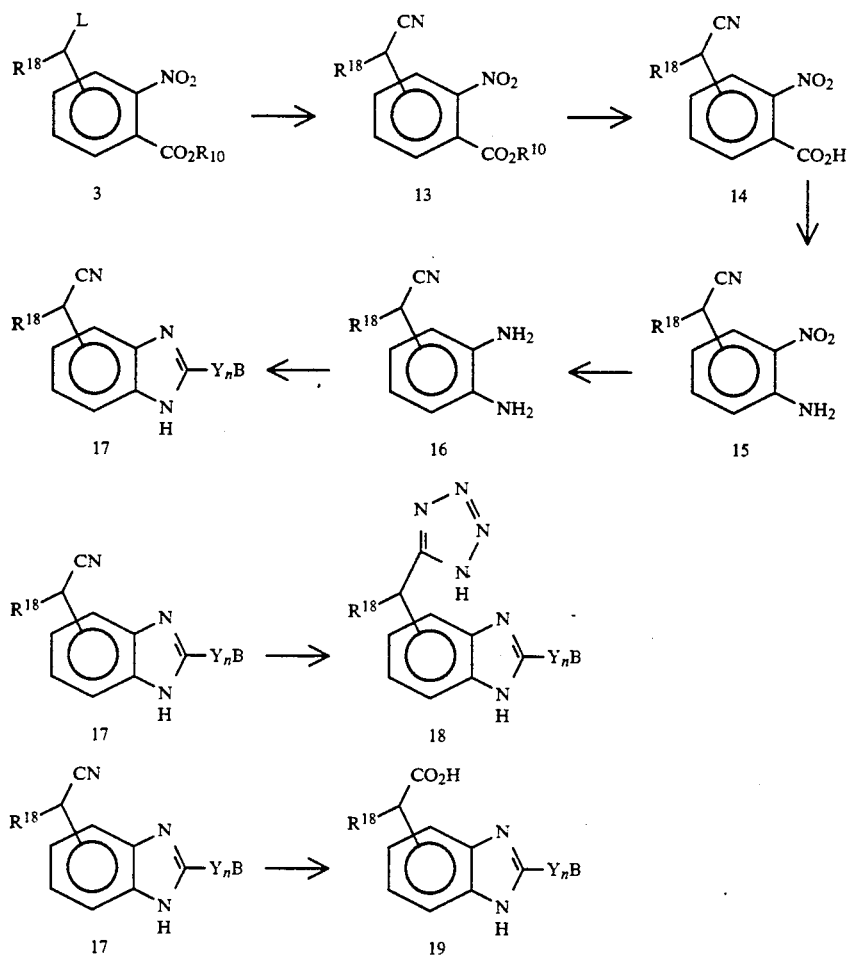
Scheme III
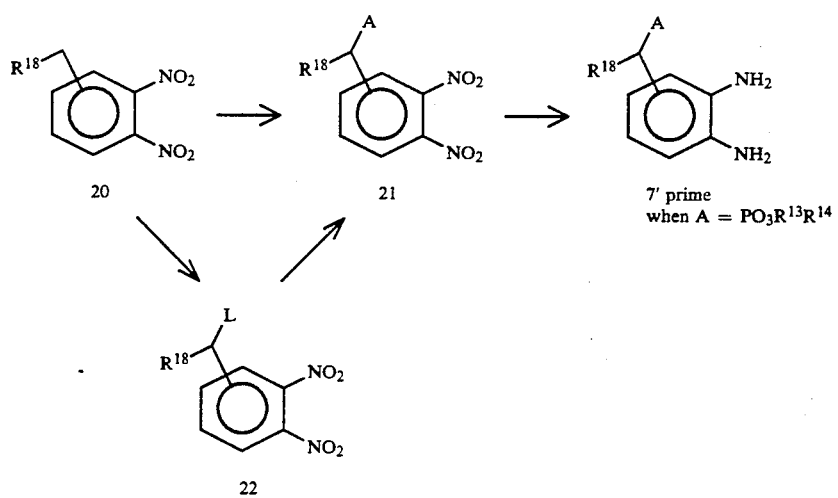
Scheme IV

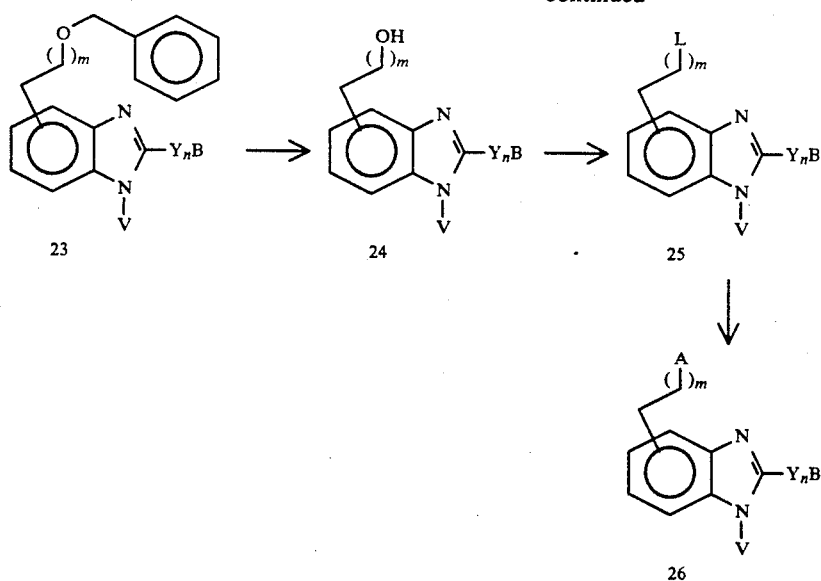

Schemes I–IV show alternative methods for preparation of compounds of the invention. These compounds can be synthesized by starting with commercially available reagents such as 2-nitro-3-methylbenzoic acid (1), 2-nitro-6-methylbenzoic acid, and various other appropriately substituted reagents recognized by those skilled in the art. Various other ring substitution patterns of functional groups are also commercially available, for example 5-methyl-2-nitrobenzoic acid (1). These allow placement of the terminal acid groups at other positions, for example aryl ring position 5, using the chemical manipulations described below. The carboxylic acid can be converted to an ester by treatment with an alcohol and HCl gas or conversion of the acid to an acid chloride or other activated esters followed by treatment with an alcohol (2). The remaining methyl or methylene group can be halogenated with $Br_2$ or N-bromosuccinimide (NBS), or N-chlorosuccimimide (NCS), or various other reagents to generate the benzylic halide. Alternatively the methyl group may be oxidized to an alcohol, or acid followed by reduction to the alcohol, and then the resulting hydroxy group converted into a good leaving group L such as bromide, chloride, tosylate, mesylate, etc. (3). The phosphonate group can be introduced using the Arbuzov reaction (4), that is by treatment of the above reagent with a trialkyl phosphite, or the metal salt of a dialkyl phosphite. Alternatively the phosphonate group may be introduced by treatment of the esterified starting materials with a strong base, such as lithium diisopropylamide (LDA) or butyl lithium, followed by quenching with a dialkyl chlorophosphate.

The benzylic halides and sulfonate esters can also be used to extend the side chain and introduce various linker groups. A cyano group (13) can be introduced using cyanide salts (Scheme II) which can serve to introduce a carboxylic acid (19) group or be transformed into a tetrazole using well known procedures in the literature (18).

The amine groups can be introduced by hydrolysis of the ester functionality using a suitable base such as lithium or sodium hydroxide (5),(14) followed by a Curtius or Schmidt reaction (6),(15), which involves activation of the acid group followed by azide and heating in the presence of an aqueous acid. Alternative methods for this conversion such as the Hofmann rearrangement and reagents such as DPPA may be employed to effect the same conversion. Other reagents such as 2,3-dinitrotoluene, for example, may also be employed varying reaction conditions and reagents as necessary (Scheme III; 20–22,7). Reduction of nitro groups may be accomplished by catalytic hydrogenation or various other reducing agents to generate the required phenylenediamines (7),(16). Conversion to the benzimidazoles can be accomplished by treatment of the diamine with a carboxylic acid, acid chloride, ester, or nitrile in the presence of a acid catalyst (8),(17). Depending on the length of the side chain and subsititents, various 2-substituted benzimidazoles can be generated. The conversion of the phenylenediamines to benzimidazoles (8) can be achieved with the phosphonate group protected as the ester or as the acid. If intact, the phophonate ester can be cleaved by refluxing with strong aqueous acid or trimethylsilyl iodide or trimethylsilyl bromide (10, $R^{13}$ and $R^{14}$=H). Nitrogen alkyl and acyl groups may also be introduced (11), as well as, carboxy esters XI. When glycolic acid is used to generate the benzimidazole (9) oxidation to the carboxylic acid can be achieved with various oxidants such as $KMnO_4$ or $Na_2CrO_3$, as well as various other oxidizing agents. If the resulting product has been carried through the synthesis as the phosphonate ester, the ester can be cleaved by treatment with TMSBr or TMSI or catalytic hydrogenation with suitable ester groups (12). Additionally, when suitably functionalized, the starting reagents may be carried through to the 2-subsitituted benzimidazoles and the terminal acid moiety introduced last (Scheme IV) An example would be the 4-(3-benzyloxypropyl)-2-carboxybenzimidazole (23), wherein cleavage of the benzyl ether using catalytic hydrogenation affords a hydroxy group (24) which can be manipulated as described above to introduce various terminal acidic groups (26). Those skilled in the art will recognize compatability requirements and reagents necessary to effect such transformations.

The following working Example shows detailed descriptions of the methods of preparation of a compound of Formula I. This detailed preparation falls within the scope of, and serve to exemplify, the above described General Synthetic Procedures which form part of the invention. This Example is presented for illustrative purposed only and is not intended as a restriction on the scope of the invention. All parts are by weight unless otherwise indicated. In Scheme V there is shown an outline of a specific method for making a compound of the invention as described in more detail in Example 1, which follows.

1H NMR data: CDCl$_3$, TMS 2.36 (s, 3H), 3.89 (s, 3H), 7.49 (m, 2H), 7.87 (d, 1H).

Step 2: Synthesis of Methyl 2-nitro-3-bromomethylbenzoate: Methyl 2-nitro-3-methylbenzoate (15.3 gm) was suspended in carbon tetrachloride (45 mL) along with N-bromosuccinimide (15 3 gm) and heated to reflux. 2,2'-Azobis(2-methylpropionitrile) (AIBN) (0.4 gm) was added to the refluxing solution in four equal portions over 48 hours. The reaction was cooled to room temperature, filtered, and concen-

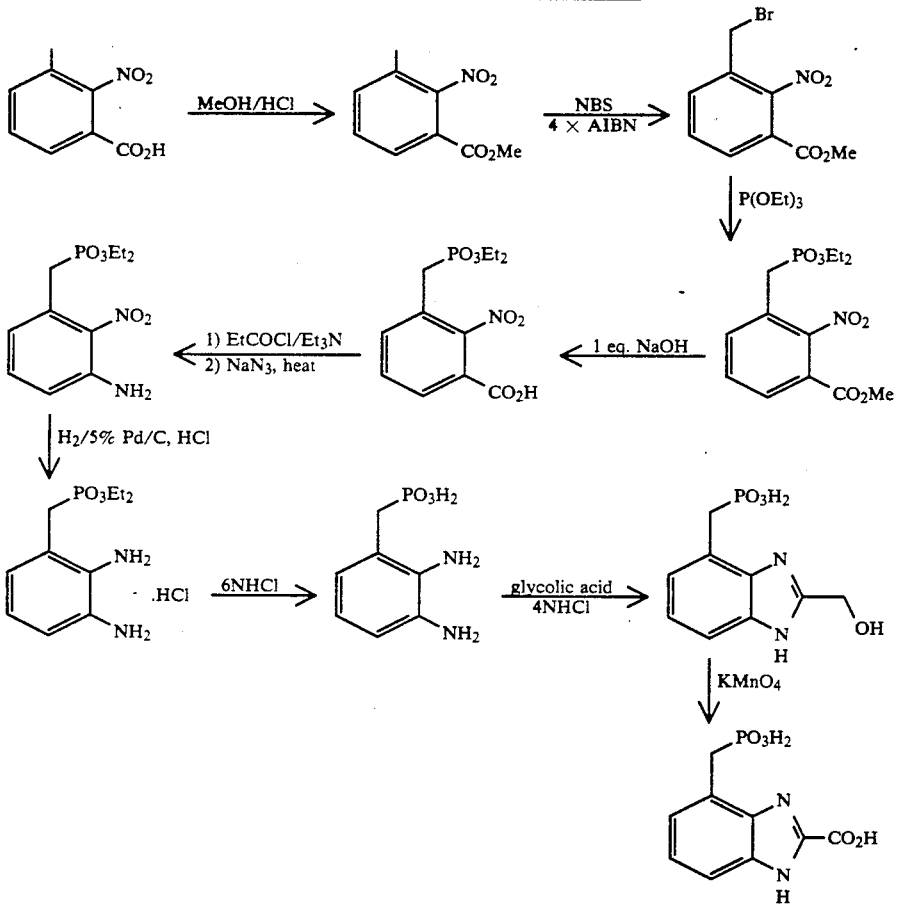

Scheme V
(Preparation of Example #1 Compound

EXAMPLE 1

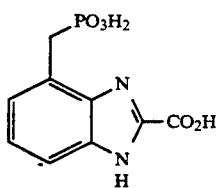

2-carboxy-4-phosphonomethylbenzimidazole.

Step 1: Synthesis of Methyl 2-nitro-3-methylbenzoate: 2-Nitro-3-methylbenzoic acid (50 gm) was dissolved in methanol (250 mL) and bubbled with HCl gas until the solution just began to reflux. The reaction mixture was stoppered and allowed to stir at room temperature for three days. The reaction was concentrated to a solid on a rotary evaporator. The solid was then redissolved and reconcentrated from methanol twice.

trated. The residue consisted of a mixture of starting material, desired product, and dibrominated material which were difficult to separate and so were used in the next step without purification.

Step 3: Synthesis of Methyl 2-nitro-3-(diethylphosphonomethyl)benzoate: The residue from above was combined with triethyl phosphite (10 mL) and heated to 110° C. for 6 hours. The excess triethyl phosphite was removed under high vacuum and the residue was chromatographed on silica (350 gm) using ethyl acetate as the eluting solvent. The unreacted methyl 2-nitro-3-methylbenzoate eluted first followed by the desired product. 1H NMR data: CDCl$_3$, TMS 1.25 (t, 6H), 3.23 (d, 2H), 3.89 (s, 3H), 4.04 ( p, 4H), 7.55 (t, 1H), 7.79 (d, 1H), 7.89 (d, 1H).

Step 4: Synthesis of 2-Nitro-3-(diethylphosphonomethyl)benzoic acid: Methyl 2-nitro-3-(diethylphosphonomethyl)benzoate (7.3 gm) was dissolved in absolute ethanol (44 mL) containing sodium hydroxide (0.89 gm) and allowed to stir at room temperature for 48 hours. The solvent was removed on a rotory evaporator and the residue dissolved in water (150 mL) and extracted with ethyl acetate (100 mL). The aqueous layer was acidified with 1N HCl and the turbid solution extracted with 3×chloroform (75 mL). The chloroform layers were combined, dried (MgSO$_4$) and concentrated to a yellow solid. 1H NMR data CDCl$_3$, TMS 1.28 (t, 6H), 3.27 (d, 2H), 4.09 (p, 4H), 7.57 (t, 1H), 7.83 (d, 1H), 7.98 (d, 1H).

Step 5: Synthesis of 2-Nitro-3-(diethylphosphonomethyl)aniline: 2-Nitro-3-(diethylphosphonomethyl)benzoic acid (5.75 gm) and triethylamine (3.2 mL) were combined in acetone (100 mL) and cooled to 0° C. in an ice bath. Ethyl chloroformate (2.2 mL) in acetone (5 mL) was added dropwise and a precipitate of triethylamine HCl began forming almost immediately. The reaction was allowed to stir for 30 minutes at 0° C. and then a solution of NaN$_3$ (1.64 gm) in water (10 mL) was added rapidly. After 1 hour the reaction mixture was partitioned between toluene (300 mL) and water (500 mL). The aqueous layer was extracted with 3×toluene (100 mL) and the combined toluene layers were in turn combined with 6N HCl (50 mL) and heated slowly to reflux with vigorous stirring. After N$_2$ evolution ceased (ca. 2 hours) the mixture was concentrated on a rotary evaporator to a solid. The solid was taken up in water (50 mL) and neutralized with saturated NaHCO$_3$, then the solution was extracted with 3×CH$_2$Cl$_2$ (50 mL). The organic extracts were combined, dried (MgSO$_4$) and concentrated to an orange solid. 1H NMR data: CDCl$_3$, TMS 1.21 (t, 6H), 3.58 (d, 2H), 4.01 (p, 4H), 4.90 (br s,2H), 6.68 (m, 2H), 7.14 (t, 1H). M.S. (E.I.) m/e 288, (m - NO$_2$) 242, (m-NO$_2$1-Et) 214, (m - Et) 186.

Step 6: Synthesis of 2-Hydroxymethyl-4-phosphonomethylbenzimidazole: 2-Nitro-3-(diethylphosphonomethyl)aniline (3.2 gm) in ethanol (60 mL) was combined with 10% Pd on carbon and concentrated HCl (ca. 1 mL) and hydrogenated at 55 psi for 3 hours. Additional ethanol was added and the mixture filtered through diatomaceous earth and concentrated to a solid. The solid was combined with 6N HCl and heated to reflux for 16 hours. The reaction was concentrated to a reddish solid combined with water and reconcentrated. The solid was then combined with glyoxalic acid (1.4 gm) and water (30 mL) and heated to reflux for 16 hours. The reaction mixture was concentrated to a solid. H NMR data: D$_2$O (HDO at 4.81 ppm) 3.26 (d,2H), 4.92 (s, 2H), 7.26 (m, 3H).

Step 7: Synthesis of 2-Carboxy-4-phosphonomethylbenzimidazole: 2-Hydroxymethyl-4-phosphonomethylbenzimidazole (411 mg) and KMnO$_4$ (70 mg) in water (7 mL) containing 3 equivalents of NaOH were warmed to 80° C. KMnO$_4$ (636 mg) was divided into 9 equal portions and added over 3.5 hours. The reaction was stirred at 80° C. for one additional hour then cooled and filtered through diatomaceous earth. The pale yellow solution was concentrated to a yellow solid. The solid was taken up in water and applied to a column of Amberlite CG 400 (0.5×16 cm). The column was eluted with water (50 mL), then 1N HOAc, 2N HOAc, 4N HOAc, and finally 1N HCl (50 mL each). The HCl fractions were pooled and concentrated to a yellow solid. The solid was triturated with water, then collected by suction filtration and washed with a small amount of ethanol and ether to obtain a white solid. H NMR data: D$_2$O (HDO at 4.64 ppm) 3.06 (d, 2H), 7.15 (m, 2H), 7.41 (d, 1H). E.A. Cal'd for C$_9$H$_9$N$_2$O$_5$P.0.6 H$_2$O; C, 40.49, H, 3.85, N, 10.49. Found; C, 40.10, N, 3.57, N, 10.30.

BIOLOGICAL EVALUATION

NMDA-Selective Glutamate Binding Assay

Synaptic plasma membranes (SPM) were prepared as previously described [Monahan, J. B. and Michel, J., "Identification and Characterization of an N-methyl-D-aspartate-specific L[$^3$H]glutamate Recognition Site in Synaptic Plasma Membranes", *J. Neurochem.*, 48, 1699–1708 (1987)]. The SPM were stored at a concentration of 10–15 mg/ml in 0.32M sucrose, 0.5 mM EDTA, 1 mM MgSO$_4$, 5 mM Tris/SO$_4$, pH 7.4, under liquid nitrogen. The identity and purity of the subcellular fractions were confirmed by both electron microscopy and marker enzymes. Protein concentrations were determined by using a modification of the method of Lowry [Ohnishi, S. T. and Barr, J. K., "A Simplified Method of Quantitating Proteins Using the Biuret and Phenol Reagents", *Anal. Biochem.*, 86, 193–197 (1978)]. The SPM were treated identically for the [$^3$H]AMPA (QUIS), [$^3$H]kainate and sodium-dependent L-[$^3$H]-glumatate binding assays. The SPM were thawed at room temperature, diluted twenty-fold with 50 mM Tris/acetate, pH 7.4, incubated at 37° C. for 30 minutes, and centrifuged at 100,000 g for 15 minutes. The dilution, incubation, and centrifugation was repeated a total of three times. Prior to use in the NMDA specific L-[$^3$H]-glutamate binding assay the SPM were thawed, diluted twenty fold with 50 mM Tris/acetate, pH 7.4 containing 0.04% (v/v) Triton X-100, incubated for 30 minutes at 37° C. and centrifuged as described above. The Triton X-100 treated membranes were washed with 50 mM Tris/acetate, pH 7.4 and centrifuged at 100,000 g for 15 minutes a total of four times. Triton X-100 treatment of the SPM resulted in a higher affinity and more consistency in this L-[$^3$H]glutamate binding assay. For this reason the K$_d$ for glutamate and the K$_i$ values for other compounds are lower than previously reported; however, the pharmacological profile of this binding site was unaltered. The basic procedure for the receptor subclass binding assays was similar. This general method involved adding the radioligand (12.5 nM L-[$^3$H] glutamate; 0.5 nM [$^3$H]kainate or 10 nM [$^3$H]AMPA) to the appropriate concentration of the test compound and initiating the assay by the addition of ice cold synaptic plasma membranes (0.2–0.45 mg). The binding assays were performed in 1.5 mL centrifuge tubes with the total volume adjusted to 1.0 mL. Additions of test compounds were made in 50 mM Tris/acetate, pH 7.4 and incubations were carried out at 0°–4° C. The incubation time for the NMDA and the AMPA binding assays was 10 minutes, for the kainate binding assay 60 minutes and for the sodium-dependent glutamate binding assay 15 minutes. The AMPA binding assay contained 100 mM KSCN and the sodium-dependent glutamate binding assay contained 150 mM sodium acetate in addition to the previously described reagents. To terminate the incubation, the samples were centrifuged for 15 minutes at 12,000 g and 4° C. in a Beckman Microfuge 12. The supernatant was aspirated and the pelleted membranes dissolved in Beckman BTS-450 tissue solubilizer for a minimum of 6 hours at room temperature. Beckman MP scintillation cocktail containing 7 mL/l acetic acid was then added and the samples counted on a Beckman LS 5800 or 3801 liquid scintillation counter with automatic corrections for quenching and counting efficiency. Nonspecific binding was defined as the residual binding in the presence of either excess L-glutamate (0.1–0.4 mM), kainate (0.01 mM), or NMDA (0.5 mM), and was 15–25% of the total binding in the NMDA binding assay, 19–27% in the AMPA binding assay, 20–30% in the kainate binding assay and 10–15% in the sodium-dependent binding assay. Radioligand binding to the synaptic plasma membranes was analyzed using Scatchard and Hill transformations and the $K_i$ values of the compounds determined using logit-log transformations. Calculations and regression analysis were performed using templates developed for Lotus 1, 2, 3 as previously described [Pullan, L. M. "Automated Radioligand Receptor Binding Analysis with Templates for Lotus", *Computer Appln. Biosci.*, 3, 131 (1987)]. Binding results are reported in Table I for compound of the invention.

[$^3$H]MK-801 Binding assay

Modulation of [$^3$H]MK-801 binding was performed using Triton X-100 (0.04% v/v) treated rat SPM that had been extensively washed. Assay incubations were at 25° C. for 30 min. and contained 5.0 nM [$^3$H]MK-801, L-glutamate (10.0 nM), and various concentrations of the tested compound in 50 mM Tris/acetate, pH 7.4. The assay was stopped by rapid filtration, using Brandel MB-48 Harvester, through Whatman GF/B filters treated with 0.05% polyethylenimine and the samples washed four times with 2.0 mL cold buffer. The radioactivity associated with the filter was determined by liquid scintillation spectrometry. Nonspecific binding was defined using 60 μM MK-801. $IC_{50}$ were determined using a logit-log transformation of the binding data. Results are reported in Table 1.

TABLE I

| Compound Ex. # | Receptor Binding Data ($IC_{50}$) | | |
|---|---|---|---|
| | [3H]GLU $K_i$ (μM) | KA $K_i$ (μM) | [$^3$H]MK-801 $K_i$ (μM) |
| 1 | 1.6 | >100 | 3.9 |

Forebrain Ischemia Assay

This assay was used to determine the extent of protection afforded by compound of the invention to neural brain cells subjected to ischemic conditions. Male Mongolian gerbils, 50–70 gm, were used as subjects. Compound Example #1 was injected i.p. 30 minutes prior to carotid occlusion into 6 gerbils at two different doses (300 mg/kg and 500 mg/kg). In preparation for surgical procedures, the animals were lightly anesthetized with methoxyflurane and placed upside down on a heated pad with their snout within a nosecone. A 70:30 mixture of nitrous oxide and oxygen containing 0.5% halothane was circulated through the nosecone to provide continuous anesthesia throughout the surgical procedure. A midline incision was made in the neck and the carotid arteries were exposed. A length of suture thread was placed under each carotid. The thread was then tightened around each carotid and pressure applied to the thread to insure flow was occluded. Flow was occluded for 4–5 minutes and then the thread was removed. The carotids were visually inspected to confirm that reflow had occurred. The wound was then closed with autoclips and the gerbils allowed to recover. Following surgery, the gerbils were kept alive for 7 days. They were anesthetized with 100 mg/kg sodium pentobarbital and perfused transcardially with saline (with heparin) followed by buffered formalin. The brain was removed, trimmed and prepared for histological processing. Sections (10 microns) were stained with thionin. At 7 days following this type of transient global forebrain ischemia, damaged neurons in the vulnerable CA1 region of the hippocampus have degenerated and been cleared away by glia. Quantification of the resulting lesion is made by counting the pyramidal cell somata in a 0.5 mm length of CA1 of the hippocampus on the section corresponding to P 1.7 mm in the gerbil brain atlas. Normal cell count in this region of the hippocampus in unoperated gerbils is 146 ±2. The effects of compound of Ex. #1 were assessed by comparing the number of neural cells found in the hippocampus of subjects treated with Ex. #1 compound with the cell number found in the appropriate control groups. The groups were compared by the Mann-Whitney U test [*Elementary Applied Statistics*, Wiley and Sons, New York (1965)]. The cell loss was significantly reduced in gerbils given compound of Ex. #1. Results are reported in Table II.

TABLE II

| Compound | Gerbil Ischemia Data # of Neurons/Field |
|---|---|
| Ex. #1 (500 mg/kg) | 137.4 |
| CONTROL | 39.8  $p < 0.005$ |
| Ex. #1 (300 mg/kg) | 44.3 |
| CONTROL | 19.8  $p < 0.01$ |

Anticonvulsant Assay

This assay was used to determine the extent of in vivo protection against convulsions afforded by compound of the invention to mice subjected to artifically-induced convulsive conditions. Naive male CD-1 mice (20–30 grams body weight) from Charles River Laboratories, Portage Mich. served as subjects. The mice had ad libitum access to food and water prior to testing and were maintained on a 12 hour light/12 hour dark schedule with testing during the light portion of the cycle. The mice were tested for motor impairment by use of the inverted screen test approximately 5 minutes prior to anticonvulsant testing. The inverted screen apparatus was similar to that described by Coughenour et al [*Pharmacol. Biochem. Behav.*, 6, 351–353 (1977)]. Mice were placed on 13×13 cm pieces of #4 wire mesh screen which were mounted horizontally. The screens were then slowly inverted. Mice that failed to climb to the tops of the inverted screens within 60 seconds were considered to have a motor impairment. Tonic hindlimb extensor seizures were then produced by application of electroconvulsive shock through concave electrodes to the eyeballs. Both the eyeballs and the electrodes were moistened with 0.9% saline to improve conductivity. The ECS stimulus was generated by use of a Grass model S48D stimulator with a Grass model CCU1A constant current unit in series with the output. Stimulation consisted of 10 msec pulses of a 60 pps single phase square wave for a duration of 200 msec. The current was held constant at 15 mA. Compound of Example #1 was suspended in a vehicle of 0.9% saline with a few drops of PG-Tween added. PG-Tween is a 1:1 mixture of propylene glycol and Tween 80. The Example #1 compound or vehicle was administered s.c. in a volume of 10 ml/kg body weight 30 minutes prior to application of the ECS stimulus. Immediately after ECS application, each mouse was observed for the presence or absence of a tonic hindlimb extensor seizure. There were 10 mice in each treatment group. The compound of Example #1 protected against tonic hindlimb extensor seizures in a dose-dependent fashion, and also impaired motor function in a similar dose range. Results are reported in Table III below.

TABLE III

| Dose Compound s.c. | Anticonvulsant Activity | |
|---|---|---|
| | Protected from ECS (% of Mice) | Exhibiting Motor Impairments (% of Mice) |
| 0 (vehicle) | 5 (n = 20) | 10 (n = 20) |
| Example #1- 56 mg/kg | | |
| Test A | 50 (n = 10) | 10 (n = 10) |
| Test B | 20 (n = 10) | 0 (n = 10) |

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of Formula II:

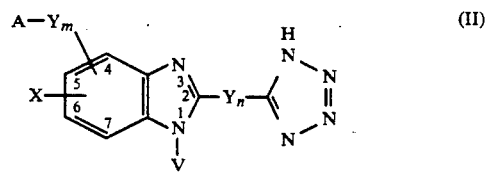

wherein A is selected from

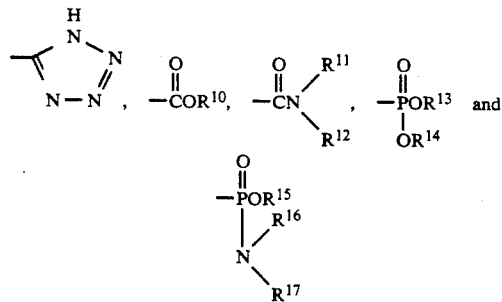

wherein each of $R^{10}$ through $R^{17}$ is independently selected from hydrido, alkyl, allyl, cycloalkyl, cycloalkylalkyl, phenyl and benzyl;
wherein each of $Y_m$ and $Y_n$ is a spacer group independently selected from one or more groups of the formula

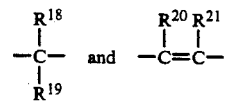

with the proviso that the total number of carbon atoms in each of $Y_m$ or $Y_n$ cannot exceed twenty carbon atoms; wherein each of $R^{18}$ and $R^{19}$ is independently selected from hydrido, alkyl, cycloalkyl, halo, haloalkyl, phenyl, benzyl, hydroxy, hydroxyalkyl, alkoxy, phenoxy, alkoxyalkyl, benzyloxy, cyano and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to four, inclusive;
wherein X is one or more groups attachable at one or more of the 4-, 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

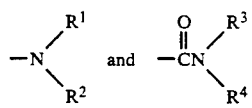 and 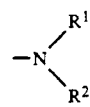

wherein each of $R^1$, $R^2$, $R^3$ and $R^4$ is independently selected from hydrido, alkyl, benzyl and phenyl;

with the further proviso that A-$Y_m$- is a single moiety attached at one of the 4-, 5-, 6- and 7-ring positions of Formula II;

wherein V is selected from hydrido, alkyl, cycloalkyl, cycloalkylalkyl, hydroxyalkyl, alkoxyalkyl, aralkyl,

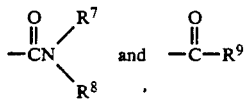

wherein each of $R^7$, $R^8$ and $R^9$ is independently selected from hydrido, alkyl, cycloalkyl, hydroxyalkyl, cycloalkyl, alkoxyalkyl and aryl; and wherein $R^9$ may be further selected from alkoxy, aryloxy and aralkyloxycarbonyl;

or a pharmaceutically-acceptable salt thereof.

2. Compound of claim 1 selected from compounds of Formula III:

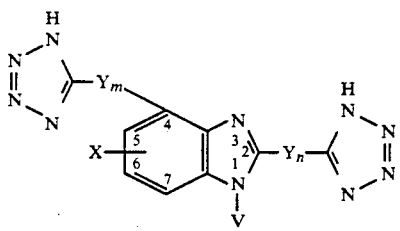

wherein each of $Y_m$ and $Y_n$ is a spacer group independently selected from one or more groups of the formula

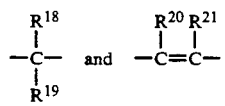

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to four, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and wherein each of $R^1$ and $R^2$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

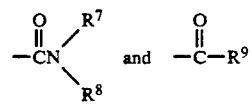

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

or a pharmaceutically-acceptable salt thereof.

3. Compound of claim 2 selected from compounds, and their pharmaceutically-acceptable salts, of the group of compounds consisting of 5-methyl-2-(1H-tetrazol-5-yl)-4-[(1H-tetrazol-5-yl)methyl]-benzimidazole;

2-(1H-tetrazol-5-yl)-4-[(1H-tetrazol-5-yl)methyl]-benzimidazole;

6-chloro-2-(1H-tetrazol-5-yl)-4-[(1H-tetrazol-5-yl)ethyl]-benzimidazole;

6-chloro-2-(1H-tetrazol-5-yl)-4-[3-(1H-tetrazol-5-yl)propyl]benzimidazole;

2-(1H-tetrazol-5-yl)-4-[3-(1H-tetrazol-5-yl)propyl]-benzimidazole;

5-methyl-2,4-bis(1H-tetrazol-5-yl)benzimidazole;

2,4-bis(1H-tetrazol-5-yl)benzimidazole;

6-chloro-2,4 bis(1H-tetrazol-5-yl)benzimidazole; and 5-methyl-2,4-bis(1H-tetrazol-5-yl)benzimidazole.

4. Compound of claim 1 selected from compounds of Formula IV:

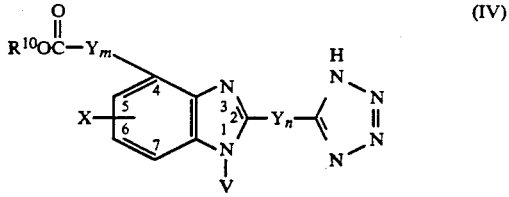

wherein each of $Y_m$ and $Y_n$ is a spacer group independently selected from one or more groups of the formula

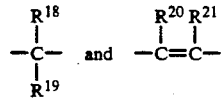

with the proviso that the total number of carbon atoms in each of Yhd m or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and R²¹ is independently selected from hydrido, alkyl, haloalkyl, phenyl, hydroxyalkyl and alkoxyalkyl; wherein each of m and n is a number independently selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

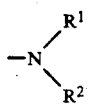

wherein each of R¹ and R² is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

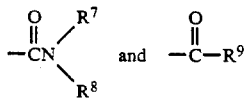

wherein each of R⁷, R⁸ and R⁹ is independently selected from hydrido, alkyl, cycloalkyl, hydroxyalkyl, cycloalkylalkyl, alkoxyalkyl and aryl; wherein R⁹ is further selected from alkoxy, phenoxy and benzyloxy;
wherein R¹⁰ is selected from hydrido, alkyl, cycloalkyl, cycloalkylalkyl, phenyl and benzyl;
or a pharmaceutically-acceptable salt thereof.

5. Compound of claim 4 selected from compounds, and their pharmaceutically-acceptable salts, of the group of compounds consisting of
2-(1H-tetrazol-5-yl)4-benzimidazolepropanoic acid;
6-chloro-2-(1H-tetrazol-5-yl)4-benzimidazolepropanoic acid;
6-chloro-2-(1H-tetrazol-5-yl)4-benzimidazolebutanoic acid;
5-methyl-2-(1H-tetrazol-5-yl)4-benzimidazoleacetic acid; and
2-(1H-tetrazol-5-yl)4-benzimidazoleactic acid.

6. Compound of claim 1 selected from compounds of Formula V:

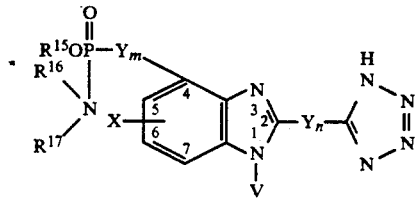

(V)

wherein each of $Y_m$ and $Y_n$ is a spacer group independently selected from one or more groups of the formula

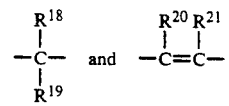

with the proviso that the total number of carbon atoms in each of $Y_m$ or $Y_n$ cannot exceed ten carbon atoms; wherein each of R¹⁸ and R¹⁹ is independently selected from hydrido, alkyl, cycloalkyl, halo, haloalkyl, hydroxy, hydroxyalkyl, alkoxy, alkoxyalkyl and alkanoyl; wherein R¹⁸ and R¹⁹ may be taken together to form oxo or exomethylene; wherein each of R²⁰ and R²¹ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

wherein each of R¹ and R² is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

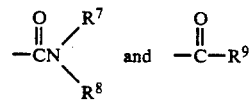

wherein each of R⁷, R⁸ and R⁹ is independently selected from hydrido, alkyl, cycloalkyl, hydroxyalkyl, cycloalkylalkyl, alkoxyalkyl and aryl; wherein R⁹ is further selected from alkoxy, phenoxy and benzyloxy;
wherein each of R¹⁵, R¹⁶ and R¹⁷ is independently selected from hydrido, alkyl, cycloalkyl, cycloalkylalkyl, phenyl and benzyl;
or a pharmaceutically-acceptable salt thereof.

7. Compound of claim 1 selected from compounds, and their pharmaceutically-acceptable salts, of the group of compounds consisting of
5-methyl-2-(1H-tetrazol-5-yl)-4-benzimidazolemethylphosphonamide;
2-(1H-tetrazol-5-yl)-4-benzimidazolemethylphosphonamide;
6-chloro-2-(1H-tetrazol-5-yl)-4-benzimidazoleethylphosphonamide;
2-(1H-tetrazol-5-yl)-4-benzimidazoleethylphosphonamide;
6-chloro-2-(1H-tetrazol-5-yl)-4-benzimidazolepropylphosphonamide;
2-(1H-tetrazol-5-yl)-4-benzimidazolepropylphosphonamide;

2-(1H-tetrazol-5-yl)-4-benzimidazolephosphonamide; and 5-methyl-2-(1H-tetrazol-5-yl)-4-benzimidazoleethyl-phosphonamide.

8. Compound of claim 1 selected from compounds of Formula VI:

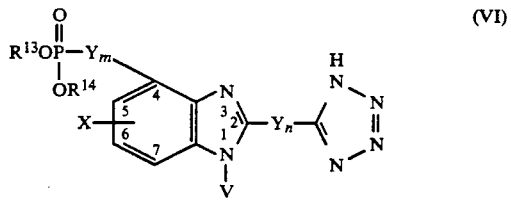

wherein each of $Y_m$ and $Y_n$ is a spacer group independently selected from one or more groups of the formula

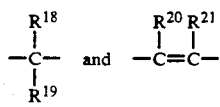

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

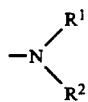

wherein each of $R^1$ and $R^2$ is independently selected from hydrido, alkyl, benzyl and phenyl;

where V is selected from hydrido, alkyl, cycloalkyl, cycloalkylalkyl, hydroxyalkyl, alkoxyalkyl, aralkyl,

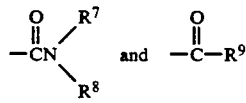

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein each of $R^{13}$ and $R^{14}$ is independently selected from hydrido, alkyl, cycloalkyl, cycloalkylalkyl, phenyl and benzyl;

or a pharmaceutically-acceptable salt thereof.

9. Compound of claim 8 selected from compounds, and their pharmaceutically-acceptable salts, of the group of compounds consisting of

[5-methyl-2-(1H-tetrazol-5-yl)benzimidazole]-4-methyl-phosphonic acid;

[2-(1H-tetrazol-5-yl)benzimidazole]-4-methylphosphonic acid;

[6-chloro-2-(1H-tetrazol-5-yl)benzimidazole]-4-ethyl-phosphonic acid;

[2-(1H-tetrazol-5-yl)benzimidazole]-4-ethylphosphonic acid;

[6-chloro-2-(1H-tetrazol-5-yl)benzimidazole]-4-propyl-phosphonic acid;

[2-(1H-tetrazol-5-yl)benzimidazole]-4-propylphosphonic acid;

[2-(1H-tetrazol-5-yl)benzimidazole]-4-phosphonic acid; and

[5-methyl-2-(1H-tetrazol-5-yl)benzimidazole]-4-ethyl-phosphonic acid.

10. A compound of Formula VII:

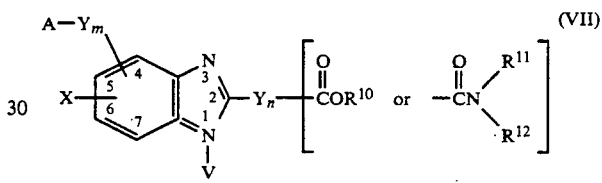

wherein A is selected from

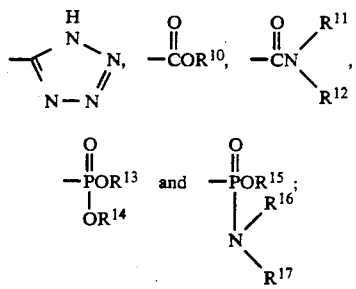

wherein each of $R^{10}$ through $R^{17}$ is independently selected from hydrido, alkyl, allyl, cycloalkyl, cycloalkylalkyl, phenyl and benzyl;

wherein each of $Y_m$ and $Y_n$ is a spacer group independently selected from one or more groups of the formula

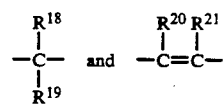

with the proviso that the total number of carbon atoms in each of $Y_m$ or $Y_n$ cannot exceed twenty carbon atoms; wherein each of $R^{18}$ and $R^{19}$ is independently selected from hydrido, alkyl, cycloalkyl, halo, haloalkyl, phenyl, benzyl, hydroxy, hydroxyalkyl, alkoxy, phenoxy, alkoxyalkyl, benzyloxy, cyano and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to three, inclusive;

wherein X is one or more groups attachable at one or more of the 4-, 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

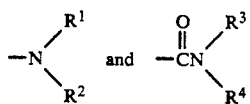

wherein each of $R^1$, $R^2$, $R^3$ and $R^4$ is independently selected from hydrido, alkyl, benzyl and phenyl;

with the further proviso that A-$Y_m$- is a single moiety attached at one of the 4-, 5-, 6- and 7-ring positions of Formula VII;

wherein V is selected from hydrido, alkyl, cycloalkyl, cycloalkylalkyl, hydroxyalkyl, alkoxyalkyl, aralkyl,

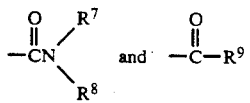

wherein each of $R^7$, $R^8$ and $R^9$ is independently selected from hydrido, alkyl, cycloalkyl, hydroxyalkyl, cycloalkylalkyl, alkoxyalkyl and aryl; and wherein $R^9$ may be further selected from alkoxy, aryloxy and aralkyloxycarbonyl;

or a pharmaceutically-acceptable salt thereof.

11. Compound of claim 10 selected from compounds of Formula VIII:

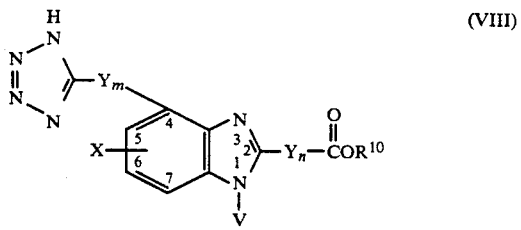

wherein each of $Y_m$ and $Y_n$ is a spacer group independently selected from one or more groups of the formula

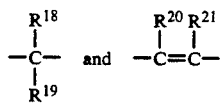

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl;

wherein each of m and n is a number independently selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

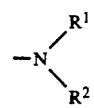

wherein each of $R^1$ and $R^2$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

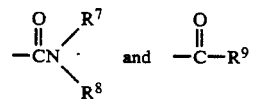

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein $R^{10}$ is selected from hydrido, alkyl, cycloalkyl, cycloalkylalkyl, phenyl and benzyl;

or a pharmaceutically-acceptable salt thereof.

12. Compound of claim 11 selected from compounds, and their pharmaceutically-acceptable salts, of the group of compounds consisting of 5-methyl-4-[(1H-tetrazol-5-yl)methyl]benzimidazole-2-carboxylic acid;

4-[(1H-tetrazol-5-yl)methyl]benzimidazole-2-carboxylic acid;

6-chloro-4-[2-(1H-tetrazol-5-yl)ethyl]benzimidazole-2-carboxylic acid;

6-chloro-4-[2-(1H-tetrazol-5-yl)ethyl]benzimidazole-2-carboxylic acid;

4-[2-(1H-tetrazol-5-yl)ethyl]benzimidazole-2-carboxylic acid;

4-[3-(1H-tetrazol-5-yl)propyl]benzimidazole-2-carboxylic acid;

6-chloro-4-[3-(1H-tetrazol-5-yl)propyl]benzimidazole-2-carboxylic acid;

5-methyl-4-(1H-tetrazol-5-yl)benzimidazole-2-carboxylic acid;

4-(1H-tetrazol-5-yl)benzimidazole-2-carboxylic acid.

13. Compound of claim 10 selected from compounds of Formula IX:

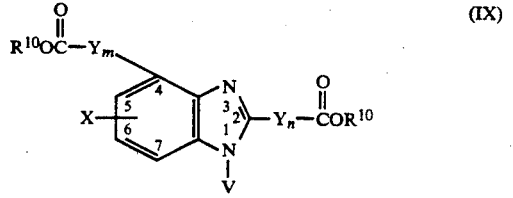

wherein each of $Y_m$ and $Y_n$ is a spacer group independently selected from one or more groups of the formula

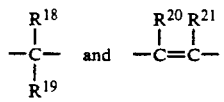

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

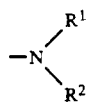

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

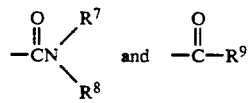

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein $R^{10}$ is selected from hydrido, alkyl, cycloalkyl, cycloalkylalkyl, phenyl and benzyl;
or a pharmaceutically-acceptable salt thereof.

14. Compound of claim 13 selected from compounds, and their pharmaceutically-acceptable salts, of the group of compounds consisting of
5-methyl-2-carboxy-4-benzimidazoleacetic acid;
2-carboxy-4-benzimidazoleacetic acid;
6-chloro-2-carboxy-4-benzimidazolepropanoic acid;
2-carboxy-4-benzimidazolepropanoic acid;
6-chloro-2-carboxy-4-benzimidazolebutanoic acid;
2-carboxy-4-benzimidazolebutanoic acid;
5-methyl-2,4-benzimidazoledicarboxylic acid; and
2,4-benzimidazoledicarboxylic acid.

15. Compound of claim 10 selected from compounds of Formula X:

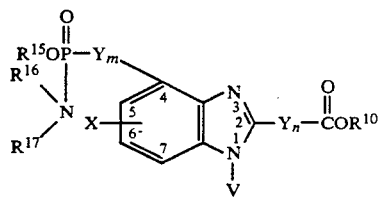

wherein each of $Y_m$ and $Y_n$ is a spacer group independently selected from one or more groups of the formula

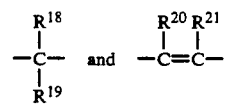

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

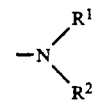

wherein each of $R^1$ and $R^2$ is independently selected from hydrido, alkyl and phenyl;
wherein V is selected from hydrido, alkyl, cycloalkyl, cycloalkylalkyl, hydroxyalkyl, alkoxyalkyl, aralkyl,

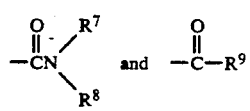

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein each of $R^{10}$, $R^{15}$, $R^{16}$ and $R^{17}$ is independently selected from hydrido, alkyl, allyl, cycloalkyl, cycloalkylalkyl, phenyl and benzyl;
or a pharmaceutically-acceptable salt thereof.

16. Compound of claim 15 selected from compounds, and their pharmaceutically-acceptable salts, of the group of compounds consisting of 4-(phosphonamidomethyl)benzimidazole-2-carboxylic acid; ethyl 4-[2-(ethoxyphosphonamido)ethyl]benzimidazole-2-carboxylate;
4-(phosphonamidoethyl)benzimidazole-2-carboxylic acid; ethyl 6-chloro-4-[(ethoxyphosphonamide)methyl]-benzimidazole-2-carboxylate;
6-chloro-4-(phosphonamidomethyl)benzimidazole-2-carboxylic acid;
ethyl 5-methyl-4-[(ethoxyphosphonamido)methyl]-benzimidazole-2-carboxylate;
5-methyl-4-(phosphonamidomethyl)benzimidazole-2-carboxylic acid;
ethyl 6-chloro-5-methyl-4-[(ethoxyphosphonamido)methyl]-benzimidazole-2-carboxylate;
6-chloro-5-methyl-4-(phosphonamidomethyl)benzimidazole-2-carboxylic acid;
ethyl 4-(ethoxyphosphonamido)benzimidazole-2-carboxylate;
ethyl 4-(ethoxyphosphonamido)benzimidazole-2-carboxylate, monohydrochloride;
4-phosphonoamidobenzimidazole-2-carboxylic acid;
ethyl 4-[2-(ethoxyphosphonamido)-E-ethenyl]-benzimidazole-2-carboxylate;
4-(2-phosphonamido-E-ethenyl)benzimidazole-2-carboxylic acid; and
4-(2-phosphonamidoethyl)benzimidazole-2-carboxylic acid.

17. Compound of claim 10 selected from compounds of Formula XI:

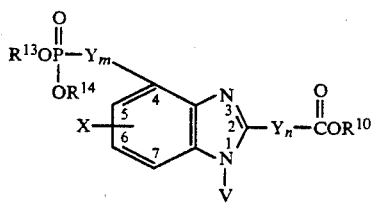

(XI)

wherein each of $Y_m$ and $Y_n$ is a spacer group independently selected from one or more groups of the formula

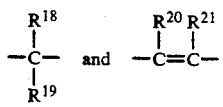

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

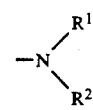

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

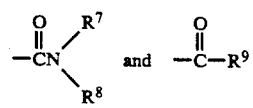

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein each of $R^{10}$, $R^{13}$ and $R^{14}$ is independently selected from hydrido, alkyl, allyl, cycloalkyl, cycloalkylalkyl, phenyl and benzyl;
or a pharmaceutically-acceptable salt thereof.

18. Compound of claim 17 selected from compounds, and their pharmaceutically-acceptable salts, of the group of compounds consisting of
2-carboxy-4-(phosphonomethyl)benzimidazole;
ethyl 4-[(diethoxyphosphonyl)ethyl]benzimidazole-2-carboxylate;
4-(phosphonoethyl)benzimidazole-2-carboxylic acid;
ethyl 6-chloro-4-[(diethoxyphosphonyl)methyl]benzimidazole-2-carboxylate;
6-chloro-4-(phosphonomethyl)benzimidazole-2-carboxylic acid;
ethyl 5-methyl-4-[(diethoxyphosphonyl)methyl]benzimidazole-2-carboxylate;
5-methyl-4-(phosphonomethyl)benzimidazole-2-carboxylic acid;
ethyl 6-chloro-5-methyl-4-[(ethoxyphosphonyl)methyl]-benzimidazole-2-carboxylate;
5-methyl-4-(phosphonomethyl)benzimidazole-2-carboxylic acid;
ethyl 4-(diethoxyphosphonyl)benzimidazole-2-carboxylate;
ethyl 4-(diethoxyphosphonyl)benzimidazole-2-carboxylate, monohydrochloride;
4-phosphonobenzimidazole-2-carboxylic acid;
ethyl 4-[2-(diethoxyphosphonyl)-E-ethenyl]benzimidazole-2-carboxylate;
4-(2-phosphono-E-ethenyl)benzimidazole-2-carboxylic acid; and
4-(2-phosphonoethyl)benzimidazole-2-carboxylic acid.

19. Compound of claim 18 which is 2-carboxy-4-(phosphonomethyl)benzimidazole or a pharmaceutically-acceptable salt thereof.

20. Compound of claim 10 selected from compounds of Formula XII:

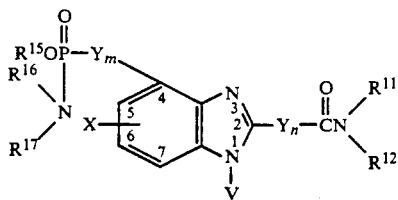

(XII)

wherein each of $Y_m$ and $Y_n$ is a spacer group independently selected from one or more groups of the formula

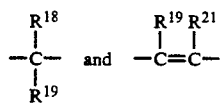

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

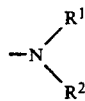

wherein each of $R^1$ and $R^2$ is independently selected from hydrido, alkyl, benzyl and phenyl;

wherein V is selected from hydrido, alkyl, cycloalkyl, cycloalkylalkyl, hydroxyalkyl, alkoxyalkyl, aralkyl,

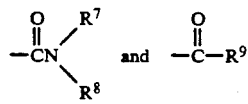

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein each of $R^{11}$, $R^{12}$, $R^{15}$, $R^{16}$ and $R^{17}$ is independently selected from hydrido, alkyl, allyl, cycloalkyl, cycloalkylalkyl, phenyl and benzyl;

or a pharmaceutically-acceptable salt thereof.

21. Compound of claim 20 selected from compounds, and their pharmaceutically-acceptable salts, of the group of compounds consisting of 4-(phosphonamidomethyl)benzimidazole-2-carboxamide;
4-[(ethoxyphosphonamido)ethyl]benzimidazole-2-carboxamide;
4-(phosphonamidoethyl)benzimidazole-2-carboxamide;
6-chloro-4-(phosphonamidomethyl)benzimidazole-2-carboxamide;
5-methyl-4-[(ethoxyphosphonamido)methyl]benzimidazole-2-carboxamide;
5-methyl-4-(phosphonamidomethyl)benzimidazole-2-carboxamide;
6-chloro-5-methyl-4-[(ethoxyphosphonamido)methyl]-benzimidazole-2-carboxamide;
6-chloro-5-methyl-4-(phosphonamidomethyl)benzimidazole-2-carboxamide;
4-(ethoxyphosphonamido)benzimidazole-2-carboxamide;
4-(ethoxyphosphonamido)benzimidazole-2-carboxamide, monohydrochloride;
4-phosphonoamidobenzimidazole-2-carboxamide;
4-[2-(ethoxyphosphonamido)-E-ethenyl]benzimidazole-2-carboxamide;
4-(2-phosphonamido-E-ethenyl)benzimidazole-2-carboxamide; and
4-(2-phosphonamidoethyl)benzimidazole-2-carboxamide.

22. Compound of claim 10 selected from compounds of Formula XII:

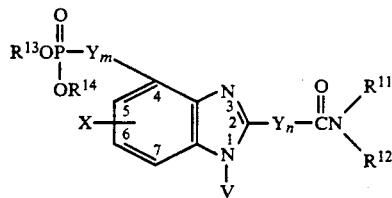

(XIII)

wherein each of $Y_m$ and $Y_n$ is a spacer group independently selected from one or more groups of the formula

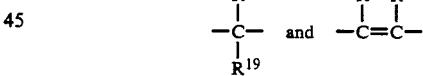

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

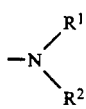

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

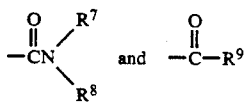

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein each of $R^{11}$, $R^{12}$, $R^{13}$ and $R^{14}$ is independently selected from hydrido, alkyl, allyl, cycloalkyl, cycloalkylalkyl, phenyl and benzyl;
or a pharmaceutically-acceptable salt thereof.

23. Compound of claim 22 selected from compounds, and their pharmaceutically-acceptable salts, of the group of compounds consisting of
4-(phosphonomethyl)benzimidazole-2-carboxamide;
4-[2-(diethoxyphosphonyl)ethyl]-benzimidazole-2-carboxamide;
4-(2-phosphonoethyl)benzimidazole-2-carboxamide;
6-chloro-4-[(diethoxyphosphonyl)methyl]benzimidazole-2-carboxamide;
6-chloro-4-(phosphonomethyl)benzimidazole-2-carboxamide;
5-methyl-4-[(diethoxyphosphonyl)methyl]benzimidazole-2-carboxamide;
5-methyl-4-(phosphonomethyl)benzimidazole-2-carboxamide;
6-chloro-5-methyl-4-[(diethoxyphosphonyl)methyl]-benzimidazole-2-carboxamide;
6-chloro-5-methyl -(phosphonomethyl)benzimidazole-2-carboxamide;
4-(diethoxyphosphonyl)benzimidazole-2-carboxamide;
4-(diethoxyphosphonyl)benzimidazole-2-carboxamide, monohydrochloride;
4-phosphonobenzimidazole-2-carboxamide;
4-[2-(diethoxyphosphonyl)-E-ethenyl]benzimidazole-2-carboxamide;
4-(2-phosphono-E-ethenyl)benzimidazole-2-carboxamide; and
4-(2-phosphonoethyl)benzimidazole-2-carboxamide.

24. Compound of claim 10 selected from compounds of Formula XIV:

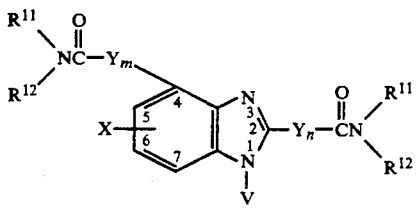

wherein each of $Y_m$ and $Y_n$ is a spacer group independently selected from one or more groups of the formula

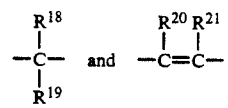

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl, wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;
wherein X is one or more groups attachable at one or more of the 5-, 6- and 7-ring positions of the benzimidazole ring system; wherein each X is independently selected from hydrido, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio and arylthio,

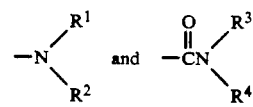

wherein each of $R^1$, $R^2$, $R^3$ and $R^4$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

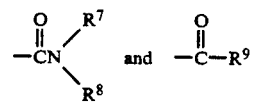

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;
wherein each of $R^{11}$ and $R^{12}$ is independently selected from hydrido, alkyl, allyl, cycloalkyl, cycloalkylalkyl, phenyl and benzyl;
or a pharmaceutically-acceptable salt thereof.

25. Compound of claim 24 selected from compounds, pharmaceutically-acceptable salts, of the group of compounds consisting of
5-methyl-2-carboxamidobenzimidazole-4-acetamide;
2-carboxamidobenzimidazole-4-acetamide;
6-chloro-2-carboxamidobenzimidazole-4-propanamide;
2-carboxamidobenzimidazole-4-propanamide;
6-chloro-2-carboxamidobenzimidazole-4-butanamide;
2-carboxamidobenzimidazole-4-butanamide;
5-methylbenzimidazole-2,4-dicarboxamide; and
benzimidazole-2,4-dicarboxamide.

26. Compound of claim 10 selected from compounds of Formula XV:

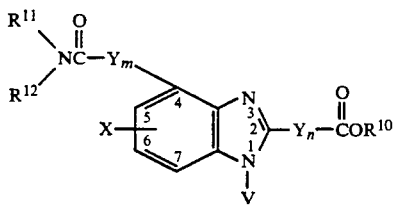
(XV)

wherein each of $Y_m$ and $Y_n$ is a spacer group independently selected from one or more groups of the formula

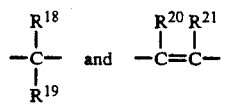

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein each of m and n is a number independently selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio and arylthio,

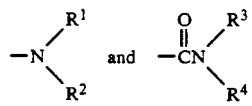

wherein each of $R^1$, $R^2$, $R^3$ and $R^4$ is independently selected from hydrido, alkyl, benxyl and phenyl;

wherein V is selected from hydrido, alkyl, cycloalkyl, cycloalkylalkyl, hydroxyalkyl, alkoxyalkyl, aralkyl,

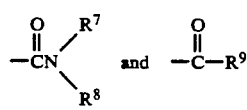

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein each of $R^{10}$, $R^{11}$ and $R^{12}$ is independently selected from hydrido, alkyl, cycloalkyl, cycloalkylalkyl, phenyl and benzyl;

or a pharmaceutically-acceptable salt thereof.

27. Compound of claim 26 selected from compounds, and their pharmaceutically-acceptable salts, of the group of compounds consisting of
5-methyl-4-acetamidobenzimidazole-2-carboxylic acid;
4-acetamidobenzimidazole-2-carboxylic acid;
6-chloro-4-propanamidobenzimidazole-2-carboxylic acid;
4-propanamidobenzimidazole-2-carboxylic acid;
6-chloro-4-butanamidobenzimidazole-2-carboxylic acid; and
4-butanamidobenzimidazole-2-carboxylic acid.

28. A pharmaceutical composition comprising a therapeutically-effective amount of an active compound and a pharmaceutically-acceptable carrier or diluent, said active compound selected from a family of compounds of Formula XI:

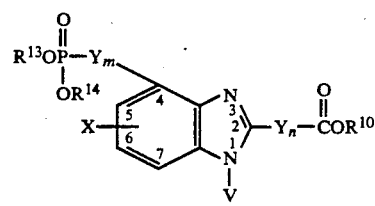
(XI)

wherein each of $Y_m$ and $Y_n$ is a spacer group independently selected from one or more groups of the formula

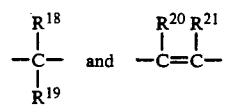

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein m is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

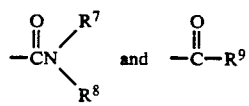

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein each of $R^{10}$, $R^{13}$ and $R^{14}$ is independently selected from hydrido, alkyl, allyl, cycloalkyl, cycloalkylalkyl, phenyl and benzyl;

or a pharmaceutically-acceptable salt thereof.

29. The composition of claim 28 wherein said active compound is slected from compounds, and their pharmaceutically-acceptable salts, of the group of compounds consisting of 2-carboxy-4-(phosphonomethyl)benzimidazole;
ethyl 4-[(diethoxyphosphonyl)ethyl]benzimidazole-2-carboxylate;
4-(phosphonoethyl)benzimidazole-2-carboxylic acid;
ethyl 6-chloro-4-[(diethoxyphosphonyl)methyl]benzimidazole-2-carboxylate;
6-chloro-4-(phosphonomethyl)benzimidazole-2-carboxylic acid;
ethyl 5-methyl-4-[(diethoxyphosphonyl)methyl]benzimidazole-2-carboxylate;
5-methyl-4-(phosphonomethyl)benzimidazole-2-carboxylic acid;
ethyl 6-chloro-5-methyl-4-[(ethoxyphosphonyl)methyl]benzimidazole-2-carboxylate;
5-methyl-4-(phosphonomethyl)benzimidazole-2-carboxylic acid;
ethyl 4-(diethoxyphosphonyl)benzimidazole-2-carboxylate;
ethyl 4-(diethoxyphosphonyl)benzimidazole-2-carboxylate, monohydrochloride;
4-phosphonobenzimidazole-2-carboxylic acid;
ethyl 4-[2-(diethoxyphosphonyl)-E-ethenyl]benzimidazole-2-carboxylate;
4-(2-phosphono-E-ethenyl)benzimidazole-2-carboxylic acid; and
4-(2-phosphonoethyl)benzimidazole-2-carboxylic acid.

30. The composition of claim 29 wherein said active compound is 2-carboxy-4-(phosphonomethyl)benzimidazole or a pharmaceutically-acceptable salt thereof.

31. A method to control neuropathological processes and the neurodegenerative consequences thereof in a subject, which method comprises treating a subject susceptible to a neurodegenerative disease or neurotoxic injury with a therapeutically-effective amount of a compound of Formula XI:

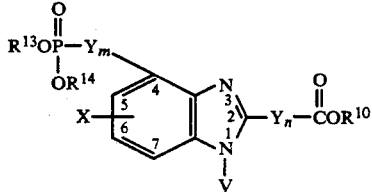

wherein each of $Y_m$ and $Y_n$ is a spacer group independently selected from one or more groups of the formula

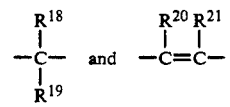

with the proviso that the total number of carbon atoms in each of $Y_m$ or $Y_n$ cannot exceed ten carbon atoms; wherein each of $R^{18}$ and $R^{19}$ is independently selected from hydrido, alkyl, cycloalkyl, halo, haloalkyl, hydroxy, hydroxyalkyl, alkoxy, alkoxyalkyl and alkanoyl; wherein $R^{18}$ and $R^{19}$ may be taken together to form oxo or exomethylene; wherein each of $R^{20}$ and $R^{21}$ is independently selected from hydrido, alkyl, haloalkyl, phenyl, hydroxyalkyl and alkoxyalkyl; wherein is a number selected from one to three, inclusive; wherein n is a number selected from zero to three, inclusive;

wherein X is one or more groups attachable at one or more of the 5-, 6- and 7-ring positions of the benzimidazole ring system; wherein each X is independently selected from hydrido, halo, alkyl, cycloalkyl, cycloalkylalkyl, haloalkyl, alkenyl, alkynyl, phenyl, benzyl, hydroxy, hydroxyalkyl, alkoxy, phenoxy, alkoxyalkyl, benzyloxy, cyano, alkanoyl, alkylthio, arylthio, and

wherein each of $R^1$ and $R^2$ is independently selected from hydrido, alkyl, benzyl and phenyl;
wherein V is selected from hydrido, alkyl, cycloalkyl, cycloalkylalkyl, hydroxyalkyl, alkoxyalkyl, aralkyl,

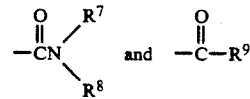

wherein each of $R^7$, $R^8$ and $R^9$ is independently selected from hydrido, alkyl, cycloalkyl, hydroxyalkyl, cycloalkylalkyl, alkoxyalkyl and aryl; wherein $R^9$ is further selected from alkoxy, phenoxy and benzyloxy;

wherein each of $R^{10}$, $R^{13}$ and $R^{14}$ is independently selected from hydrido, alkyl, allyl, cycloalkyl, cycloalkylalkyl, phenyl and benzyl;

or a pharmaceutically-acceptable salt thereof.

32. The method of claim 31 wherein said compound is selected from compounds, and their pharmaceutically-acceptable salts, of the group of compounds consisting of 2-carboxy-4-(phosphonomethyl)benzimidazole;
ethyl 4-[(diethoxyphosphonyl)ethyl]benzimidazole-2-carboxylate;
4-(phosphonoethyl)benzimidazole-2-carboxylic acid;
ethyl 6-chloro-4-[(diethoxyphosphonyl)methyl]benzimidazole-2-carboxylate;
6-chloro-4-(phosphonomethyl)benzimidazole-2-carboxylic acid;
ethyl 5-methyl-4-[(diethoxyphosphonyl)methyl]benzimidazole-2-carboxylate;
5-methyl-4-(phosphonomethyl)benzimidazole-2-carboxylic acid;

ethyl 6-chloro-5-methyl-4-[(ethoxyphosphonyl)methyl]benzimidazole-2-carboxylate;

5-methyl-4-(phosphonomethyl)benzimidazole-2-carboxylic acid;

ethyl 4-(diethoxyphosphonyl)benzimidazole-2-carboxylate;

ethyl 4-(diethoxyphosphonyl)benzimidazole-2-carboxylate, monohydrochloride;

4-phosphonobenzimidazole-2-carboxylic acid;

ethyl 4-[2-(diethoxyphosphonyl)-E-ethenyl]benzimidazole-2-carboxylate;

4-(2-phosphono-E-ethenyl)benzimidazole-2-carboxylic acid; and 4-(2-phosphonoethyl)benzimidazole-2-carboxylic acid.

33. The method of claim 32 wherein said compound is 2-carboxy-4-(phosphonomethyl)benzimidazole or a pharmaceutically-acceptable salt thereof.

34. The method of claim 31 for use in treating a neurodegenerative disease.

35. The method of claim 31 for use in treating or reducing neurotoxic injury.

36. The method of claim 35 for use in treating neurotoxic injury resulting from ischemia.

37. The method of claim 35 for use in reducing neurotoxic injury resulting from an hypoxic or anoxic condition.

38. The method of claim 37 wherein said hypoxic or anoxic condition arises from stroke, cardiac arrest or perinatal asphyxia.

* * * * *